United States Patent [19]
Vale et al.

[11] Patent Number: 6,147,275
[45] Date of Patent: Nov. 14, 2000

[54] CORTICOTROPIN RELEASING FACTOR RECEPTOR 1-DEFICIENT MICE

[75] Inventors: Wylie Vale, La Jolla; Kuo-Fen Lee, Del Mar, both of Calif.

[73] Assignee: Research Development Foundation, Carson City, Nev.

[21] Appl. No.: 09/281,150

[22] Filed: Mar. 30, 1999

Related U.S. Application Data

[60] Provisional application No. 60/079,874, Mar. 30, 1998, abandoned.

[51] Int. Cl.[7] .................................................. A01K 62/027
[52] U.S. Cl. .............................................................. 800/18
[58] Field of Search ................................ 800/3, 8, 13, 18

[56] References Cited

PUBLICATIONS

Theiler (in: The House Mouse, Atlas of Embryonic Development, Springer–Verlag, publishers, see pp. 148 and 149, 1989.

Primary Examiner—Bruce R. Campell
Assistant Examiner—Richard Schnizer
Attorney, Agent, or Firm—Benjamin Aaron Adler

[57] ABSTRACT

Signaling pathways dependent on members of the corticotropin releasing factor (CRF) gene family exert pleiotropic effects within both the brain and peripheral tissues. Two biochemically and pharmacologically distinct corticotropin releasing factor receptor subtypes (corticotropin releasing factor receptor-1 and corticotropin releasing factor receptor-2) have been described. To study the developmental and physiological role of the specific receptor subtypes, a strain of mice null for the corticotropin releasing factor receptor-1 gene has been generated. This genetically engineered strain of mice suggest that corticotropin releasing factor receptor-1 is obligatory both in development and function of the hypothalamic-pituitary-adrenal axis and in mediating behavioral changes associated with anxiety and locomotor activity rhythms.

10 Claims, 15 Drawing Sheets

(3 of 15 Drawing Sheet(s) Filed in Color)

CORTICOTROPIN RELEASING FACTOR RECEPTOR 1-DEFICIENT MICE

CROSS-REFERENCE TO RELATED APPLICATIONS

This application claims benefit of U.S. provisional application Ser. No. 60/079,874, filed Mar. 30, 1998, now abandoned.

FEDERAL FUNDING LEGEND

This invention was produced in part using funds obtained through grant DK-26741 from the National Institutes of Health. Consequently, the federal government has certain rights in this invention.

BACKGROUND OF THE INVENTION

1. Field of the Invention

The present invention relates generally to the fields of endocrinology and neuroendocrinology. More specifically, the present invention relates to the corticotropin releasing factor receptor-1 and animals deficient in the corticotropin releasing factor receptor-1 receptor.

2. Description of the Related Art

Survival of an organism is dependent on maintenance of homeostasis in response to stressful conditions. Homeostasis is maintained through adaptational responses geared to counteract the effects of aversive stimuli (Chrousos et al., 1992). Generally, these adaptive responses result from the stimulation of neural pathways linked to self protection, such as attention, arousal and aggression, and the inhibition of pathways that promote vegetative functions such as growth, reproduction and feeding (Chrousos et al., 1992). In mammals, corticotropin releasing factor (CRF) is a major integrator of the endocrine, neuroendocrine, autonomic and behavioral responses to stress (Owens & Nemeroff, 1991; Vale et al., 1981). Dysregulation of the stress response results in quite severe psychological and physiological consequences. Indeed, chronic hyperactivation of the corticotropin releasing factor system has been linked to many affective disorders, such as anxiety, anorexia nervosa and melancholic depression (Chrousos et al., 1992; Orth, 1992).

In addition to its role in the stress response, corticotropin releasing factor is also implicated in the control of cognitive function. Corticotropin releasing factor is known to increase learning and memory in rodents (Behan et al., 1995, Diamant & de Wied, 1993, Koob & Bloom, 1985, Liang & Lee, 1988) and alterations in the corticotropin releasing factor system are associated with several neurodegenerative diseases such as Alzheimer's disease and Parkinson's disease (De Souza, 1995). However, the developmental and physiological actions of corticotropin releasing factor dependent pathways involved in these stress related phenomena and in cognitive function are not completely understood.

The pleiotropic nature of the corticotropin releasing factor system was recently expanded with the discovery of urocortin (UCN), a second mammalian member of the corticotropin releasing factor family. Urocortin, characterized from rat midbrain, shares only 45% sequence similarity with corticotropin releasing factor (Vaughan et al., 1995). While the exact function of urocortin is not known, this peptide can mimic many of the biological actions of corticotropin releasing factor in vitro and in vivo (Spina et al., 1996; Turnbull et al., 1996; Vaughan et al., 1995), although with a different potency profile.

The biological actions of corticotropin releasing factor family members are mediated via binding to specific high affinity membrane receptors belonging to the subfamily of G-protein coupled receptors for small ligands including secretin, vasoactive intestinal polypeptide and growth hormone releasing factor (Segre & Goldring, 1993). Two distinct corticotropin releasing factor receptor subtypes, corticotropin releasing factor receptor-1 and corticotropin releasing factor receptor-2, have been characterized from several species (Grigoriadis et al., 1996; Vale et al., 1997). Corticotropin releasing factor receptor-1 and corticotropin releasing factor receptor-2 share approximately 71% amino acid sequence similarity (Grigoriadis et al., 1996; Vale et al., 1997) and are both pharmacologically distinct and unique in their expression patterns within the brain and in peripheral tissues. In the adult, expression of corticotropin releasing factor receptor-1 is limited primarily to regions of the brain including the brain stem, cerebellum, cerebral cortex, and medial septum and also to the pituitary gland (Chalmers et al., 1995; Potter et al., 1994).

In contrast, corticotropin releasing factor receptor-2 is expressed in several peripheral tissues including the heart, skeletal muscle, gastrointestinal tract and the epididymis (Kishimoto et al., 1995; Lovenberg et al., 1995; Perrin et al., 1995; Stenzel et al., 1995), and expression within the brain is most prevalent in the lateral septum and hypothalamic areas (Chalmers et al., 1995; Perrin et al., 1995). While each receptor subtype can bind both corticotropin releasing factor and urocortin, urocortin displays an approximately 40 fold higher affinity for corticotropin releasing factor receptor-2 than does corticotropin releasing factor (Vaughan et al., 1995). These results suggest that urocortin may be the putative endogenous ligand for corticotropin releasing factor receptor-2. However, the specific corticotropin releasing factor receptor molecules that trigger each of the various adaptive responses to averse stimuli have not been clearly established.

The developmental role of the various components of the corticotropin releasing factor system has not been fully elucidated. Expression of corticotropin releasing factor is temporally and spatially regulated during embryonic and neonatal development and mice null for the corticotropin releasing factor gene display endocrine and developmental abnormalities (Muglia et al., 1995). In addition, corticotropin releasing factor receptors are present within distinct regions of the rat brain as early as embryonic day 15 and expression is developmentally regulated during early neonatal life (Avishai-Eliner et al., 1996; Insel et al., 1988). However, the presence of multiple corticotropin releasing factor receptor subtypes and additional corticotropin releasing factor related ligands necessitates a systematic evaluation of the biological pathways mediated by each corticotropin releasing factor receptor subtype.

Thus, the prior art is deficient in understanding the role of the corticotropin releasing factor system, the corticotropin releasing factor receptor subtypes in development and animals deficient in the corticotropin releasing factor receptor-1 receptor. The present invention fulfills this longstanding need and desire in the art.

SUMMARY OF THE INVENTION

To dissect the specific developmental and biological roles of corticotropin releasing factor receptor mediated pathways, mice deficient in corticotropin releasing factor receptor-1 were generated via homologous recombination in embryonic stem cells. Corticotropin releasing factor receptor-1 was found to be absolutely required both for development of the adrenal gland and for a normal endocrine response to stress. In addition, corticotropin releasing factor receptor-1 mutant mice showed a decreased anxiety response and an altered circadian rhythm of locomotor activity. The corticotropin releasing factor receptor-1 deficient mice provide a useful model system for characterization of the corticotropin releasing factor receptor subtypes involved in the various adaptive responses to stress and in cognitive function.

Targeted disruption of the corticotropin releasing factor receptor-1 gene clearly demonstrated a specific developmental role for corticotropin releasing factor receptor-1 in allowing sufficient ACTH secretion for postnatal maturation and function of the corticosteroid producing region of the adrenal gland. Mutation of the corticotropin releasing factor receptor-1 gene also firmly established the key role of this receptor in mediating the endocrine and behavioral responses to stress and revealed a new role of corticotropin releasing factor receptor-1 dependent pathways in modulation of locomotor activity rhythms. Delineation of the precise contribution of other members of the corticotropin releasing factor system, both in development and in maintenance of homeostasis, requires generation of animals with mutations in other components of the corticotropin releasing factor signaling pathways, which can then be crossed with the strain of mice described in the present invention.

One object of the present invention is to provide a transgenic mouse deficient in the corticotropin releasing factor receptor-1.

In one embodiment of the present invention, there is provided a method of producing a transgenic mouse having a substantial deficiency in the corticotropin releasing factor receptor-1.

In yet another embodiment of the present invention, there is provided a method by which an agonist or antagonist of corticotropin releasing factor, urocortin or related ligands that act through receptors other than corticotropin releasing factor receptor-1 may be identified.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1A: (Upper) Genomic organization of the corticotropin releasing factor receptor-1 gene showing exons 4–13. (Middle) Targeting construct utilized for homologous recombination. The HindIII-XbaI fragment (exons 5–8), encoding the last twelve amino acids of the first extracellular domain through the fourth transmembrane domain, was deleted and replaced with a PGK-neo cassette. (Bottom). The resulting mutated locus following homologous recombination. FIG. 1B: The disrupted corticotropin releasing factor receptor-1 allele was identified by Southern analysis with a BamHI-HindIII external probe which detected a 8.0 kb wild-type band and a 6.3 kb mutated band, respectively; J1 (parental ES cell line), J1-corticotropin releasing factor receptor-1 +/– (ES clone heterozygous for the mutation). FIG. 1C: corticotropin releasing factor stimulated ACTH secretion by monolayer cultures of whole pituitaries collected from wild type and corticotropin releasing factor receptor-1 mutant mice (corticotropin releasing factor receptor-1 –/–).

FIG. 2A: Markedly reduced plasma corticosterone concentrations in corticotropin releasing factor receptor-1-deficient mice. Blood samples were collected from male and female wild type and corticotropin releasing factor receptor- 1 mutant mice (corticotropin releasing factor receptor-1–/–) mice in the morning (6 AM) and the afternoon (4 PM) and plasma corticosterone concentrations determined (mean±SEM; ***P<0.001). FIG. 2B: Pronounced atrophy of adrenal glands of corticotropin releasing factor receptor-1 mutant mice. Adrenal glands of female wild type and corticotropin releasing factor receptor-1 –/– mice were sectioned and stained with hematoxylin and eosin. Note the marked hypoplasia of the zona fasciculata (ZF) region where corticosterone is produced. The zona glomerulosa (ZG), zona reticularis (Z receptor-), and medullary (M) regions were relatively unaffected. FIG. 2C: Corticotrope development in corticotropin releasing factor receptor-1 mutant mice. Pituitary glands from both wild type and corticotropin releasing factor receptor-1 –/– mice were sectioned and corticotropes were localized with anti-ACTH antibodies. No difference in the number of corticotropes was observed. (A) anterior pituitary, (I) intermediate lobe.

FIG. 5A: Total time (seconds) mice spent out of the chamber (mean±SEM; * P<0.05). Acute locomotor activity of wild type and mutant mice in a novel environment was also determined. (FIG. 5B) Total zone entries (mean±SEM) of wild type and mutant mice over a 5 min period during the light cycle. Corticotropin releasing factor receptor-1 mutant mice exhibited altered locomotor activity rhythms. FIG. 5C: Time course of locomotor activity (zone entries per hour) of corticotropin releasing factor receptor-1 mutant and wild type mice during the light and dark phase of the light-dark cycle. FIG. 5D: Basal locomotor activity (total zone entries/12 h) of wild type and mutant mice during the light and dark phases (mean±SEM; *P<0.05).

FIG. 6A: Wild-type lungs show thin alveolar septae and normal air space expansion. FIG. 6B: Mutant lungs display alveolar collapse (*) and reactive emphysema with intra-alveolar hemorrhage and hemosiderotic deposition. Hyaline membranes are not evident. FIG. 6C: Lungs from mutant neonates treated in utero with corticosterone in maternal drinking water.

FIG. 7A: Hematoxylin and eosin stained sections of adrenals collected from wild type and corticotropin releasing factor receptor-1 deficient mice on postnatal day 3 demonstrating no difference in adrenal morphology during the early postnatal period. FIG. 7B: Adrenal glands collected from corticotropin releasing factor receptor-1 −/− mice treated twice daily from postnatal days 10–21 with ACTH or diluent alone. Note the increased size and thickness of the zona fasciculata region of the adrenal gland from corticotropin releasing factor receptor-1 mutant mice treated with ACTH. FIG. 7C: Plasma ACTH concentrations on day 10 of postnatal life in samples collected from corticotropin releasing factor receptor-1 −/− or wild type mice (Mean±SEM; ** P<0.02).

DETAILED DESCRIPTION OF THE INVENTION

Figure 1A:
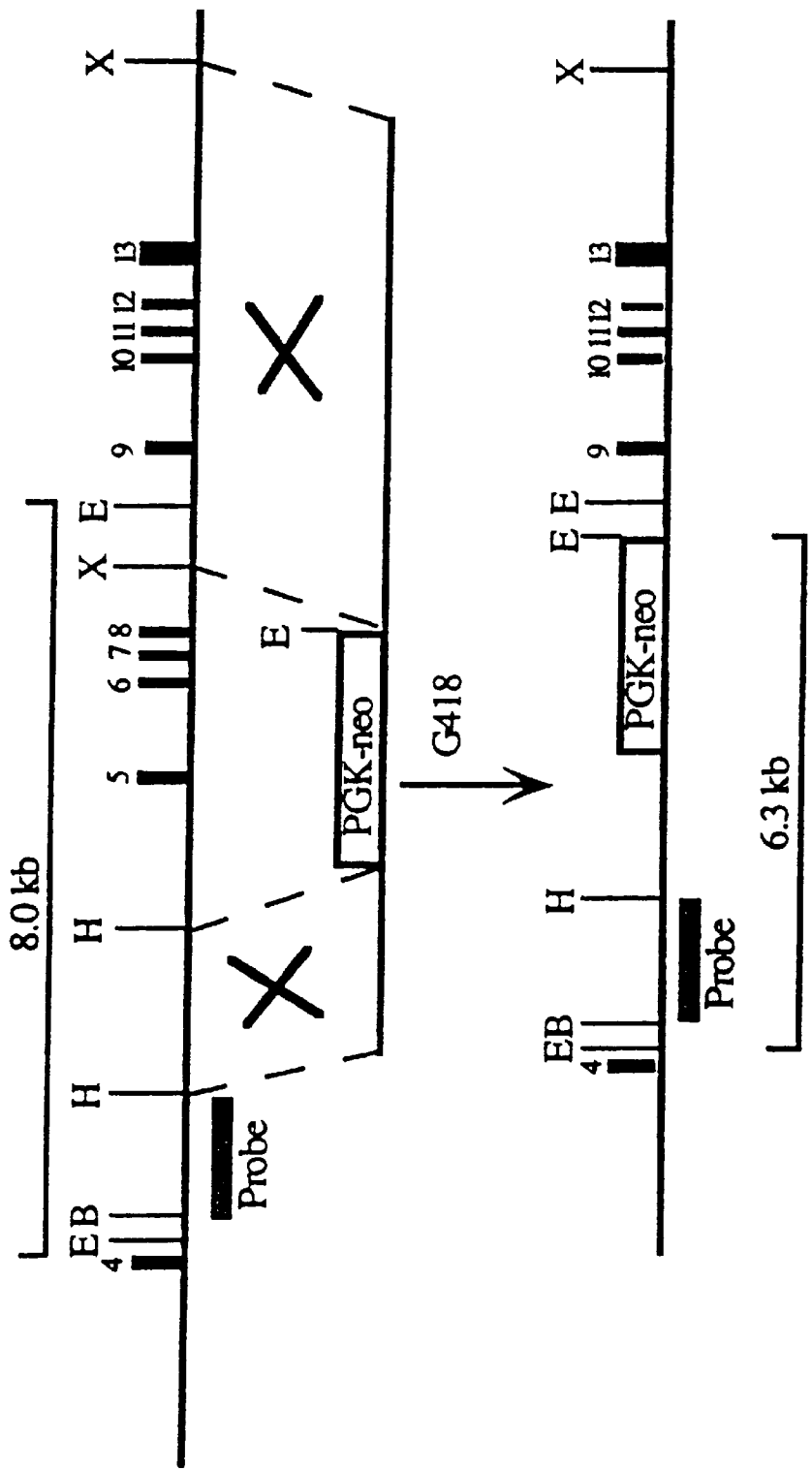
FIGS. 1A–1C shows the generation of the corticotropin releasing factor receptor-1-deficient mice.

In accordance with the present invention, there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in cells, usually termed "selectable marker genes" or "selectable markers". The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes.

Prokaryotic promoters contain Shine-Dalgarno sequences in addition to the −10 and −35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must b e sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence. "Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant", a "recombinant molecule", or a "transgene".

A cell has been "transformed", "transfected" or "transduced" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene which encodes a maize starch synthase enzyme of the present invention can be used to transform a host using any of the techniques commonly known to those of ordinary skill in the art. One preferred embodiment is the use of a vectors containing coding sequences for a gene for purposes of prokaryotic transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A standard Northern blot assay can be used to ascertain the relative amounts of mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of a gene in transgenic systems, in accordance with conventional Southern hybridization techniques known to those of ordinary skill in the art. Both the Northern blot and Southern blot use a hybridization probe, e.g. radiolabelled cDNA, or a fragment of DNA sequence at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

The present invention is directed towards a transgenic mouse deficient in the corticotropin releasing factor receptor-1 is provided. This deficiency results in a mouse with decreased anxiety, reduced endocrine response to stress and altered locomoter activity rhythms compared to a control mouse. This mouse may subsequently be mated with a mouse of another strain to produce progeny.

The present invention is also directed towards a method by which an agonist or antagonist of corticotropin releasing factor, urocortin or related ligands that act through receptors other than corticotropin releasing factor receptor-1 may be identified. The method comprises administering a test compound or a placebo to a transgenic mouse deficient in the corticotropin releasing factor receptor-1 and determining the effect of the test compound or placebo on the level of anxiety, the endocrine response to stress and the locomoter activity rhythms in the mouse. An alteration in the level of anxiety, the endocrine response to stress or locomoter activity rhythms is indicative of an agonist or antagonist of corticotropin releasing factor, urocortin or related ligands acting through a receptor other than corticotropin releasing factor receptor-1. These other receptors may include the corticotropin releasing factor receptor-2 or novel corticotropin releasing factor receptors, The present invention is also directed to a method of producing a transgenic mouse having a substantial deficiency in the corticotropin releasing factor receptor-1. This method comprises producing positive ES cells by introducing a corticotropin releasing factor receptor-1 transgene derived from a mouse corticotropin releasing factor receptor-1 gene into embryonic stem cells. The transgene comprises a gene encoding a selectable marker in place of exon 5 through exon 8 of the corticotropin releasing factor receptor-1 gene, wherein the ES cells that survive and grow under selection with the selectable marker are positive ES cells and transgenic mice are generated by introducing the positive ES cells into C57BL/6 blastocysts. These transgenic mice may be mated to produce a transgenic mouse which is homozygous for the transgene.

The present invention is also directed towards a method of screening compounds that are analogs or agonists of corticosterone or corticotropin. This method comprises performing a mating between a homozygous female mouse and a homozygous male mouse, both of which are deficient in the corticotropin releasing factor receptor-1, administering the compound to the female mouse post-conception and determining the histological condition of the lungs of progeny born to the female mouse. An absence of displaysia, alveolar collapse and reactive emphysema with intraalveolar hemorrhage and hemosiderotic deposition is indicative of an analog or agonist of corticosterone or corticotropin.

The present invention is also directed towards a method of alleviating fetal respiratory distress syndrome, consisting of administering a pharmaceutically acceptable dose of corticosterone in utero to a fetus suspected of having fetal respiratory distress syndrome.

The following examples are given for the purpose of illustrating various embodiments of the invention and are not meant to limit the present invention in any fashion:

EXAMPLE 1

Targeting Vector Construction, ES Cell Culture and Verification of Null Mutation Cloned genomic DNA corresponding to the corticotropin releasing factor receptor-1 locus was isolated from a mouse strain 129 genomic DNA library. A targeting construct was generated whereby exons 5–8 of the corticotropin releasing factor receptor-1 gene encoding the last twelve amino acids of the first extracellular domain through the fourth transmembrane domain were replaced by a PGK-neo cassette (FIG. 1). The resulting plasmid DNA was linearized with NotI and electroporated into J1 embryonic stem (ES) cells as described (Lee et al., 1992). After selection in 0.2 mg/ml of G418 for 7–9 days, neomycin resistant clones were individually selected and 50% of the cells from each clone were expanded in 96 well plates for freezing and the remaining 50% in 24 well plates for DNA isolation.

Figure 1B:
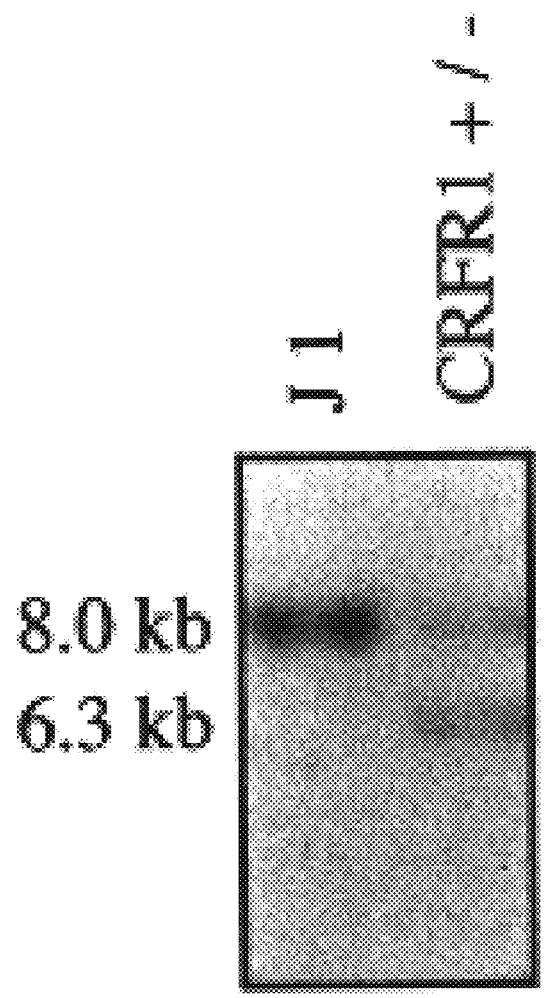

Colonies were screened for the presence of the disrupted corticotropin releasing factor receptor-1 allele by Southern analysis using an external BamHI/HindIII genomic fragment that hybridized 5' to the targeting construct (FIG. 1A). ES cell clones containing the 6.3 kb Eco receptor-I fragment diagnostic of homologous recombinants were obtained at a frequency of 1 out of 83. Cells from positive ES clones were injected into C57BL/6 blastocysts and chimeric mice generated as described (Lee et al., 1992). Germline transmission of the mutant allele was determined by Southern analysis of tail DNA collected from F1 pups displaying agouti coat color (FIG. 1B). The presence of the deletion in the corticotropin releasing factor receptor-1 gene was also confirmed by receptor-T-PC receptor- analysis of cerebellum receptor-NA isolated from homozygous mutant mice and from wild type mice using primers complementary to exons 6 and 8(the deleted region). GAPDH mRNA was amplified as a positive control for all reactions.

Primary cultures of mouse whole pituitary cells were used to verify the deletion in the corticotropin releasing factor receptor-1 gene resulted in a null mutation. Briefly, whole pituitaries were collected from 8–10 week old female mutant and control mice (approximately 10 mice per group) and dispersed as described (Vale et al., 1983). The cells were then washed in complete medium (bPJ) supplemented with 2% FBS and established as monolayers ($1.2 \times 10^5$ cells/well/ 0.5 ml) in 48 well Costar plates pre-coated with poly-d-lysine (20 μg/ml). After 3 days of recovery, the cells were equilibrated for 2 hours in bPJ medium containing 0.1% BSA and treated for 1 hour with 0–100 nM corticotropin releasing factor in fresh medium. The medium was collected and ACTH secretion was measured using a radioimmunoassay kit (Diagnostic Products Corporation).

EXAMPLE 2

Histological, Immunohistochemical and In situ Hybridization Analyses

For histological analyses, mutant and wild type mice (approximately 8–10 weeks of age unless specified otherwise) were perfused with 4% paraformaldehyde and tissues were dissected (lungs, adrenal glands, etc.) and post-fixed for 24 hours at 4° C. Tissues were subsequently embedded in paraffin, sectioned at 7 mm thickness and stained with hematoxylin and eosin prior to evaluation. For immunohistochemical localization of corticotropin releasing factor, AVP and urocortin within the brain and of ACTH within the pituitary gland, animals were perfused with 4% paraformaldehyde and tissues were sectioned at 30 mm thickness. Immunohistochemical localization of corticotropin releasing factor and AVP (Chan et al., 1993), urocortin (Vaughan et al., 1995) and ACTH (Potter et al., 1994) was conducted. For in situ hybridization analyses, mice were anesthetized and perfused with saline, followed by 4% paraformaldehyde in 0.1 M borate buffer. Tissues were stored overnight at 4° C. in fixative containing 10% sucrose. Frozen sections (30 mm thickness) were cut on a receptor-eichert microtome and stored in antifreeze solution (30% polyethylene glycol, 20% glycerol in 0.05M $NaPO_4$) until use. Hybridization and washing conditions were conducted as described (Potter et al., 1994). For in situ localization of corticotropin releasing factor mRNA, $^{35}S$ labeled antisense and sense cRNA probes were synthesized from a rat corticotropin releasing factor cDNA template (provided by Dr. Kelly Mayo, Northwestern University). For corticotropin releasing factor receptor-2 hybridizations, $^{33}P$ labeled antisense and sense cRNA probes were synthesized from approximately 1 kb of the mouse corticotropin releasing factor receptor-2 cDNA (Perrin et al., 1995) containing 80 bp of the 5' untranslated region and 926 bp of the coding sequence.

EXAMPLE 3
Blood Collection and Hormone Analyses

For all hormone analyses, animals (approximately 8–10 weeks of age unless specified otherwise) were housed individually overnight in draped cages prior to collection of blood samples by retroorbital eye bleeding. Blood samples were collected within forty five seconds of initial disturbance of the cage and samples were immediately placed on ice into tubes containing EDTA. Plasma samples were stored at −20° C. prior to analysis. For determination of corticosterone concentrations under undisturbed conditions, blood samples were collected at 6:00 AM from male and female mutant and wild type mice (n=14 each). Samples were also collected at 4 PM from male and female mutant and control mice (n=6, 6, 5 and 6, respectively). For evaluation of the endocrine response to stress, blood samples were collected at 8:00 AM from male and female corticotropin releasing factor receptor-1 mutant and wild type mice (n=6 per group). Animals were then immediately subjected to a brief physical restraint stress (10 minutes restraint in a 50 ml conical tube with the bottom removed). Then, a second blood sample was collected and animals were sacrificed immediately thereafter. For determination of circulating ACTH concentrations during the early postnatal period, plasma samples were collected from corticotropin releasing factor receptor-1 deficient (n=5) and wild type mice (n=7) on postnatal day 10. Plasma concentrations of ACTH were determined using a human ACTH two-site immunoradiometric assay (Nichols Institute, San Juan Capistrano, Calif.) using rat ACTH (1-39) as the standard. Plasma concentrations of corticosterone were determined using a rat/mouse $^{125}I$ corticosterone radioimmunoassay kit (ICN Biomedicals, Costa Mesa, Calif.) .

EXAMPLE 4
Behavioral Analyses

The behavioral response of corticotropin releasing factor receptor-1 deficient mice in an anxiogenic environment was tested using a dark-light emergence task and compared to that of control mice (n=6 male mice per group). Mice used for behavioral experiments were all singly housed. Testing was conducted in a white open-field (50×50 cm) containing a small opaque chamber 12 cm deep and 8 cm in diameter (Takahashi et al., 1989). The chamber was situated in the middle of the open-field, with the opened end facing the corner. The open-field was illuminated by a lamp directed to the center of the field (120 lux on the floor). Testing was conducted in a room with constant background white noise (80 dB). Mice were habituated to the experimental room for 1 hour, prior to the behavioral testing. Behavioral testing consisted of introducing the mice into the unfamiliar test environment by placing them into the small chamber. Behavior for a 5 min test duration was recorded with a video camera. The latency to exit the chamber, defined as the placement of all four paws in the open-field, the total time spent out of the chamber, the number of exits and the mean time spent in the open-field per exit were quantified from the video recording.

Locomotor activity was measured in large Plexiglas cages (42×22×20 cm) placed into frames (25.5×47 cm) mounted with photocell beams (San Diego Instruments, San Diego, Calif.). The horizontal locomotion frames consist of a 4×8 array of beams. Locomotor activity was tested in a room with constant background white noise (80dB; Xu et al., 1994) and similar light conditions as described above. Mice were brought into the testing room 1 hour prior to the start of the testing. The pattern of photobeam breaks was analyzed to yield the number of zone entries over time. Zone entries were defined as movement into one of 8 equal-sized squares (2×4 matrix, 11×10.5 cm/zone). This measure was used to more accurately reflect horizontal locomotion rather than the repeated breaking of a single beam.

Locomotor response in this novel environment, tested during the light phase of the cycle, was used as a control for locomotor activity in the anxiety test. The locomotor response was recorded for 180 minutes and the first 5 minutes were evaluated for comparison with the 5 minute dark-light emergence task. Two months later, locomotor activity was recorded for 48 hours, with food and water available. Basal locomotor activity was considered as the 24 hours period following a 12 hour habituation to the activity cages. The locomotor response was recorded during each phase, and the percentage of increase in activity during the dark as compared to the light phase of the cycle was calculated.

Student's t-test was used to compare the two group's locomotor activity scores and factorial analyses of variance with repeated measures (ANOVA) with group (wild type and mutant animals) as a between-subjects factor and time-course of locomotor activity as a within subject factor were performed. In the dark-light emergence task, comparisons between the groups were performed with the Mann-Whitney U test.

EXAMPLE 5
In utero Corticosteroid Rescue of Lung Dysplasia

Homozygous corticotropin releasing factor receptor-1 male and female mice were inter-crossed and mating was confirmed by the presence of a copulation plug (designated embryonic day 0). Beginning on embryonic day 12, pregnant females were treated with 25 μg/ml corticosterone (Sigma, St Louis, Mo.) in the drinking water through postnatal day 14 for assessment of neonatal survival. Lungs from corticosterone treated mutant mice, nontreated mutant mice and untreated control mice were also collected on postnatal day 1 for histological analyses as described above.

EXAMPLE 6
Hormonal Rescue of Adrenal Defect of corticotropin releasing factor receptor-1 Deficient Mice Mutant offspring born using the corticosterone rescue strategy described above were used to determine the effects of ACTH replacement on maturation of the adrenal gland. Briefly, from postnatal days 10–21, animals were injected subcutaneously twice daily with either 10 ng/g body weight of rat ACTH in diluent (0.1 M Phosphate buffer, 0.1% bovine serum albumin, 0.01 % ascorbic acid, pH 7.3), or with diluent alone. Then, adrenal glands from ACTH treated mutant mice (n=4) and from mutant mice treated with diluent only (n=3) were collected and processed as described above.

EXAMPLE 7
Generation of Corticotropin Releasing Factor Receptor-1 Deficient Mice To generate corticotropin releasing factor receptor-1 deficient mice, a targeting vector was constructed in which the portion of the corticotropin releasing factor receptor-1 gene encoding the last twelve amino acids of the first extracellular domain through the fourth transmembrane domain was replaced with a neomycin resistance gene cassette (FIG. 1A). Translation of the resulting disrupted corticotropin releasing factor receptor-1 mRNA would, therefore, result in a receptor protein incapable of incorporation into the cell membrane and, hence, nonfunctional. Six of five hundred neomycin resistant colonies screened were positive as assessed by Southern analysis with an external probe (FIG. 1B). Cells from two of the targeted ES cell lines were injected into C57 BL/6 blastocysts to generate chimeric founder mice and germline transmission of the disrupted allele was obtained. In general, homozygous mutant mice born from mating of heterozygotes developed normally and were fertile. However, a 15% mortality rate in the male corticotropin releasing factor receptor-1 mutant mice was observed. The death loss occurred primarily when animals were between 3 and 12 weeks of age and was not observed in female corticotropin releasing factor receptor-1 deficient mice nor in control mice. RT-PC receptor-analysis of mRNA collected from the cerebellum of homozygous mutant animals confirmed the presence of the deletion within the corticotropin releasing factor receptor-1 gene (data not shown).

Figure 1C:
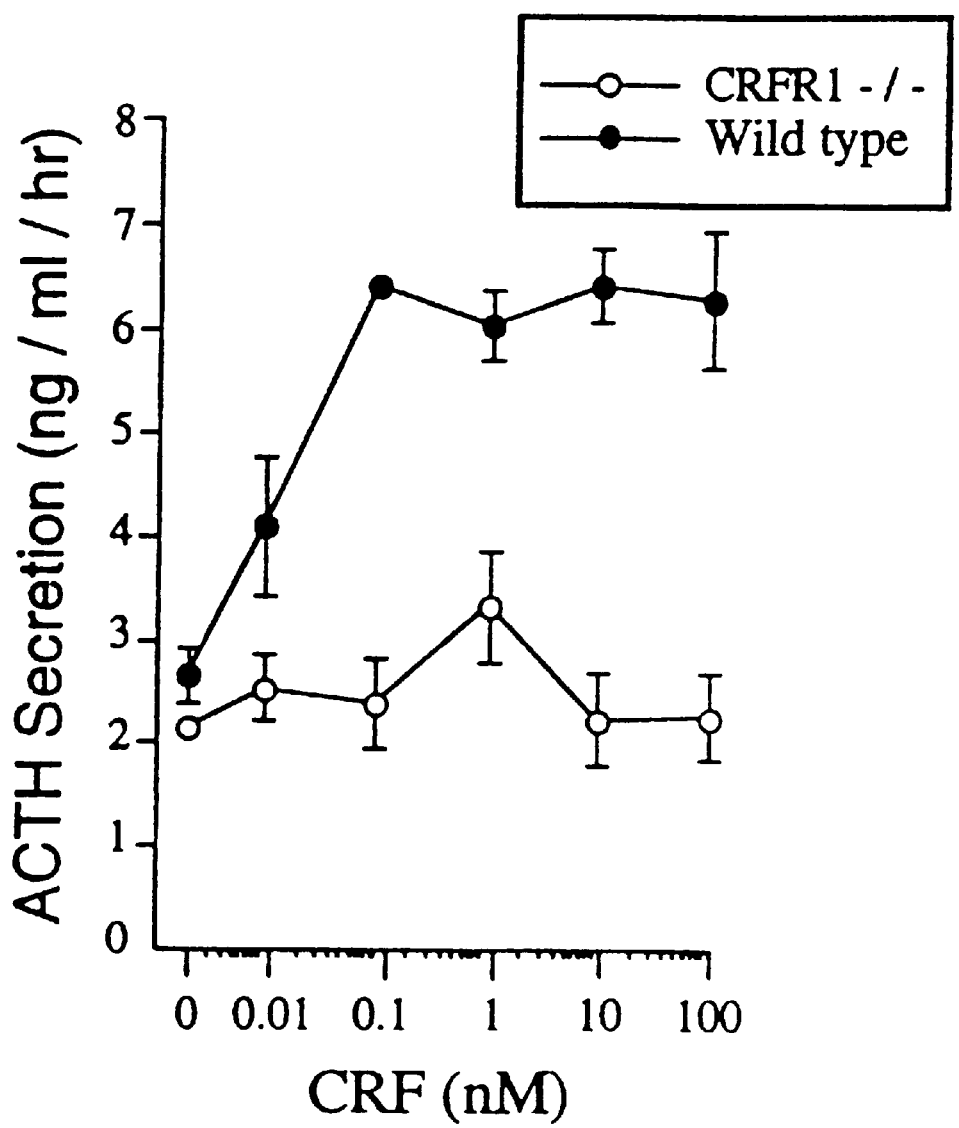

To determine whether the deletion in the corticotropin releasing factor receptor-1 gene led to a null mutation, cultured pituitary cells from wild type and mutant mice were treated for 1 hour with 0 to 100 nM corticotropin releasing factor and the levels of ACTH in culture medium were measured. Corticotropin releasing factor treatment of wild type pituitary cells resulted in a dose dependent increase in ACTH secretion (FIG. 1C). In contrast, treatment of corticotropin releasing factor receptor-1-deficient pituitary cells with 0 to 100 nM corticotropin releasing factor did not increase ACTH secretion (FIG. 1C). Thus, the targeted mutation resulted in a disrupted corticotropin releasing factor receptor-1 gene which does not produce a functional receptor protein.

Figure 2A:
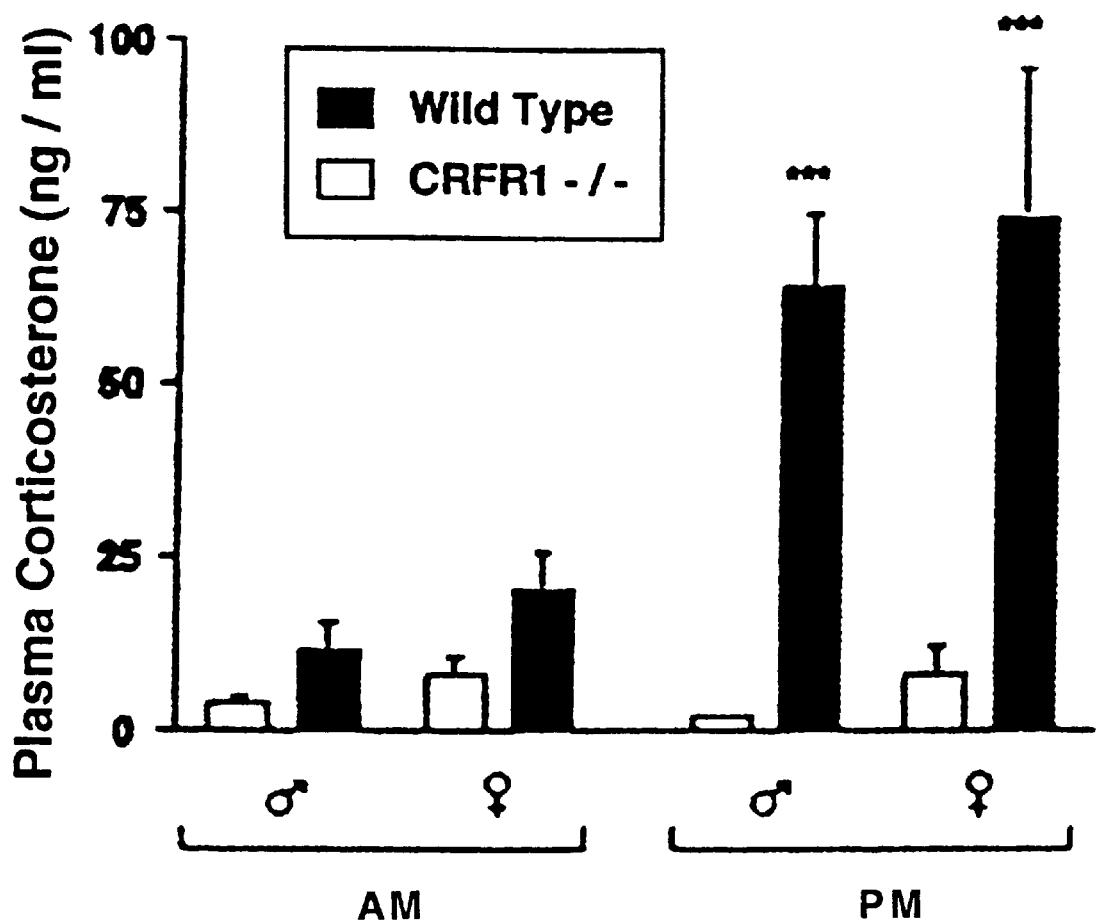
FIGS. 2A–2C show the adrenal deficiency of corticotropin releasing factor receptor-1 mutant mice.
Figure 2B:
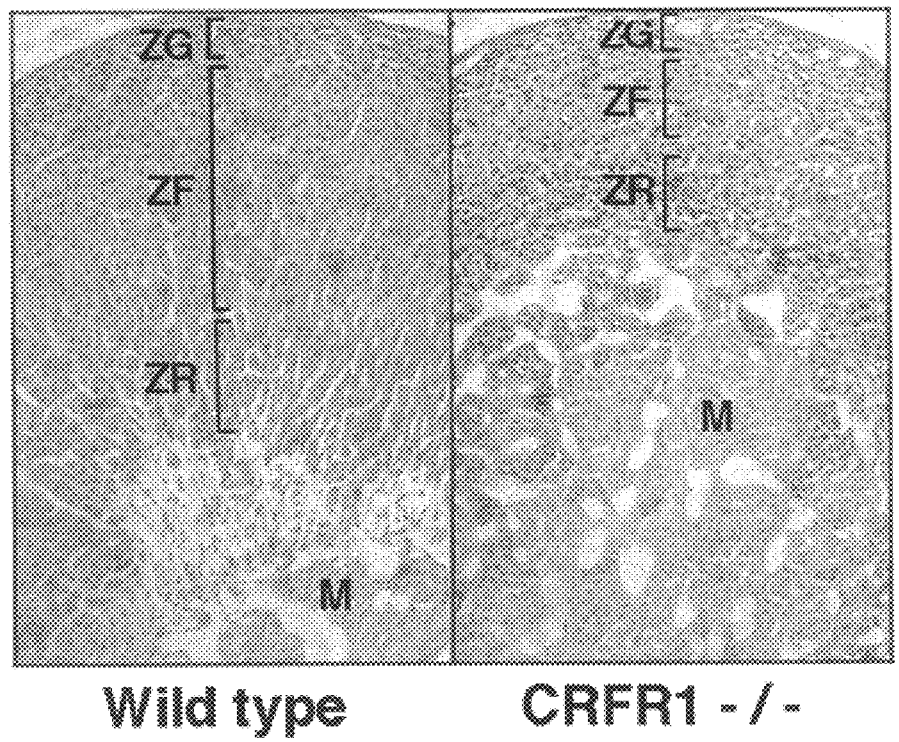

EXAMPLE 8
Mice Lacking Corticotropin Releasing Factor Receptor-1 Display a Pronounced Adrenal Deficiency Corticotropin releasing factor dependent pathways are known to play a key role in the regulation of the hypothalamic-pituitary-adrenal (HPA) axis and in many central responses to stress (Owens & Nemeroff, 1991). As an initial assessment of the function of the HPA axis in mutant animals, plasma samples were collected from male and female wild type and mutant mice at 6:00 AM and 4:00 PM. Corticotropin releasing factor receptor-1 mutants (male and female) had very low plasma corticosterone concentrations as compared to wild type mice. In particular, the characteristic diurnal rise in circulating corticosterone that occurs in the afternoon was absent in the mutant mice (FIG. 2A). Histological analysis of adrenal glands collected from corticotropin releasing factor receptor-1 deficient mice revealed the anatomical basis for the observed endocrine deficiency. Mutant animals displayed a marked atrophy of the zona fasciculata, the region of the adrenal gland which is responsible for corticosterone production (FIG. 2B). In contrast, the zona glomerulosa, the zona reticularis and the medulla of the adrenal glands of mutant mice appeared normal. Furthermore, plasma concentrations of aldosterone of mutant mice, produced by the zona glomerulosa region of the adrenal gland, were similar to those of wild type mice (data not shown). Therefore, the adrenal deficiency in corticotropin releasing factor receptor-1 deficient mice appears specific to the corticosterone producing region of the adrenal gland.

Figure 2C:
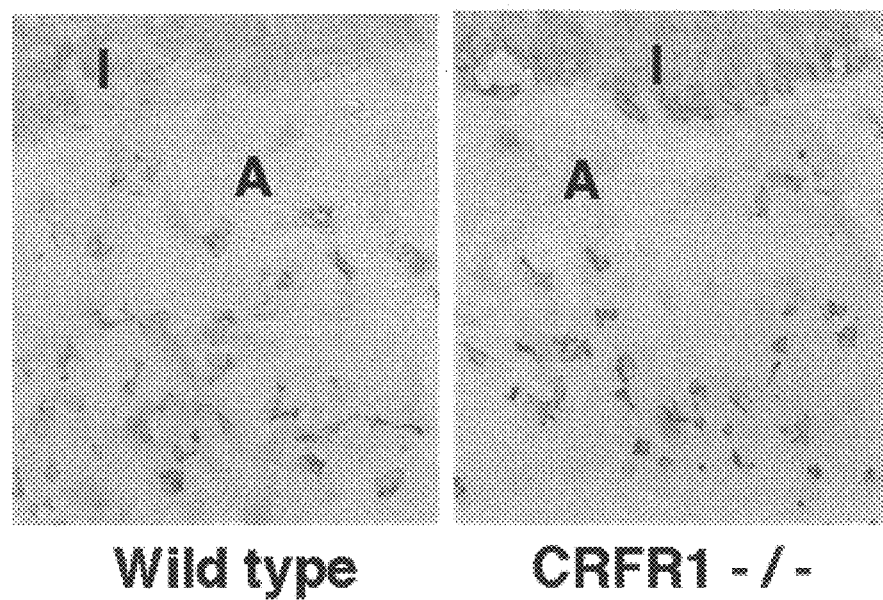

Corticotropin releasing factor can stimulate proliferation of corticotropes (ACTH producing cells of the pituitary; Gertz et al., 1987) in vivo, and pituitary ACTH is trophic for the corticosterone producing region of the adrenal gland (Idelman, 1970). Therefore, the gross morphology and cellular composition of pituitary glands from mutant mice was examined to determine if a defect in corticotrope development was evident. Histological and immunocytochemical analyses of pituitaries from mutant mice revealed no observable anatomical defects (data not shown) and a normal complement of corticotropes (FIG. 2C). Basal ACTH secretion in vitro (FIG. 1C) and the ACTH content of dispersed pituitary cells from mature mutant mice were similar to those of wild type mice. Furthermore, basal ACTH concentrations in the circulation of mutant mice during the AM (see FIG. 4B) and the PM were not different from control mice. Examination of Nissl stained sections of various regions of the brain, including the septum, hippocampus and amygdala, of corticotropin releasing factor receptor-1 deficient mice also did not reveal any obvious anatomical defects.

Figure 3A:
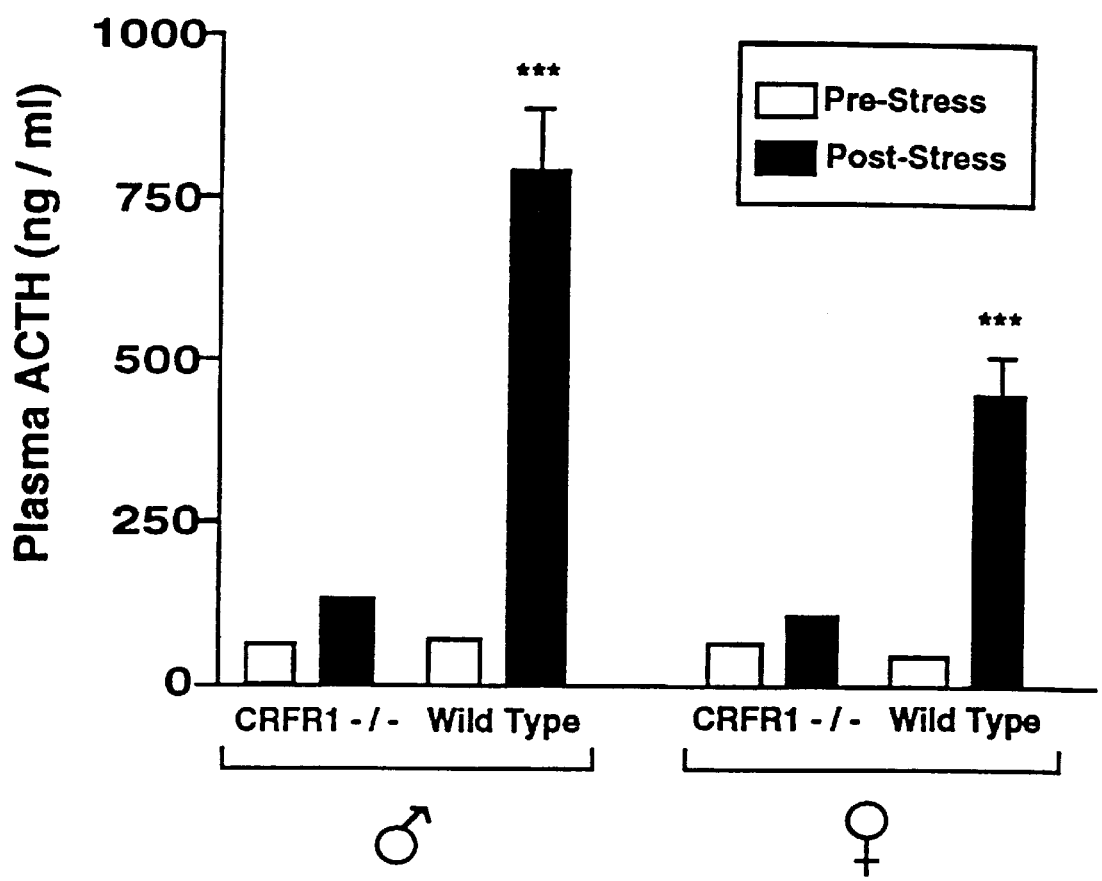
FIGS. 3A and 3B show increased expression of corticotropin releasing factor but not arginine vasopressin within the hypothalamus of corticotropin releasing factor receptor-1 deficient mice. Immunohistochemical localization of corticotropin releasing factor (FIG. 3A) and arginine vasopressin (FIG. 3B) in the paraventricular nuclei of the hypothalamus (PVN) of wild type and corticotropin releasing factor receptor-1 –/– mice revealed increased corticotropin releasing factor expression in the mutant animals. Within other corticotropin releasing factor producing regions of the brain, such as the amygdala, expression was not increased (data not shown).

EXAMPLE 9
Increased Expression of Corticotropin Releasing Factor in the Paraventricular Nuclei of the Hypothalamus of Corticotropin Releasing Factor Receptor-1 Deficient Mice Corticotropin releasing factor receptor-1 is the predominant corticotropin releasing factor receptor subtype expressed in the pituitary gland and within regions of the brain involved in mediating many of the various biological actions of corticotropin releasing factor (Grigoriadis et al., 1996). Loss of corticotropin releasing factor receptor-1 dependent pathways in mutant animals may potentially be compensated for by changes in the localization and or level of expression of other components of the corticotropin releasing factor system. Therefore, immunohistochemical and in situ hybridization analyses were conducted to characterize changes in expression of other key components of the corticotropin releasing factor system within the brains and the pituitary glands of corticotropin releasing factor receptor-1 deficient mice. Immunohistochemical analyses revealed that expression of corticotropin releasing factor within the paraventricular nuclei of the hypothalamus (PVN) of corticotropin releasing factor receptor-1 deficient mice was markedly increased in comparison to that of wild type mice (FIG. 3A). Increased corticotropin releasing factor mRNA expression was also detected with the PVN of mutant mice in comparison to that of wild type mice.

Figure 3B:
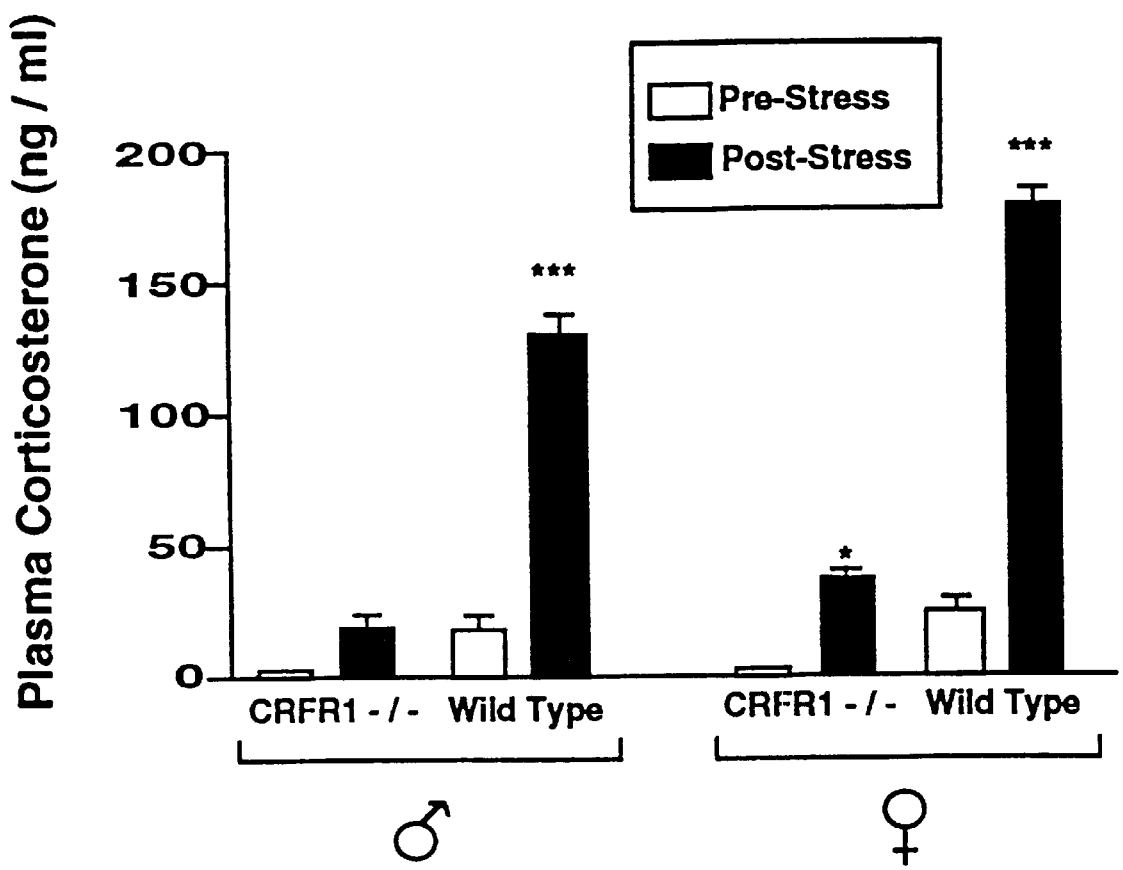

Arginine vasopressin (AVP), originating predominantly from the same neurons in the paraventricular nuclei that synthesize corticotropin releasing factor, is also a key regulator of corticotrope function. In contrast to corticotropin releasing factor, no detectable alteration in AVP expression was observed within the paraventricular nuclei of mutant mice (FIG. 3B). In other regions of the brain which produce corticotropin releasing factor, such as the amygdala, corticotropin releasing factor expression in mutant mice was not different from controls. Therefore, corticotropin releasing factor receptor-1 deficiency leads to increased corticotropin releasing factor expression specifically within the paraventricular nuclei of mutant mice. No changes in spatial distribution or levels of corticotropin releasing factor receptor-2 expression were observed in the brains or the pituitary glands of mutant mice. Likewise, central expression of urocortin within the midbrain of mutant mice was similar to that of controls.

EXAMPLE 10

Figure 4A:
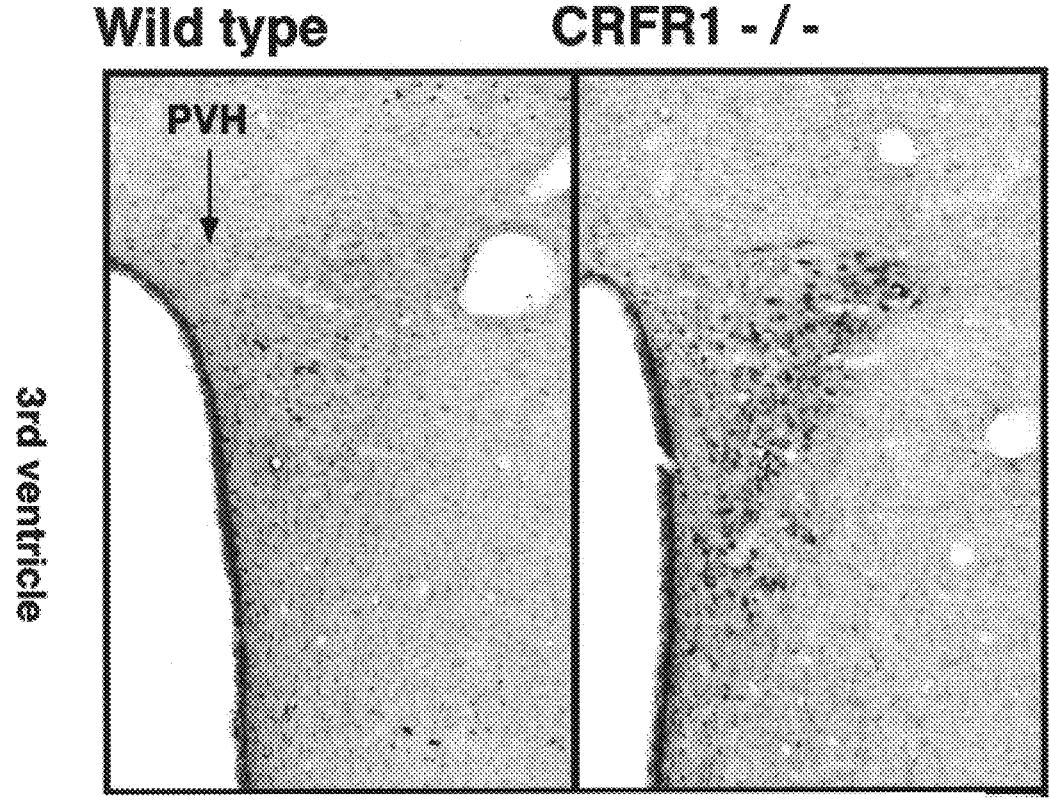
FIGS. 4A and 4B show the reduced endocrine response to stress in the corticotropin releasing factor receptor-1 deficient mice. Both sexes of wild type and mutant mice were subjected to a physical restraint for 10 minutes and the basal and post-stress levels of ACTH (FIG. 4A) and corticosterone (FIG. 4B) were measured (mean±SEM; * P<0.05, *** P<0.001).
Figure 4B:
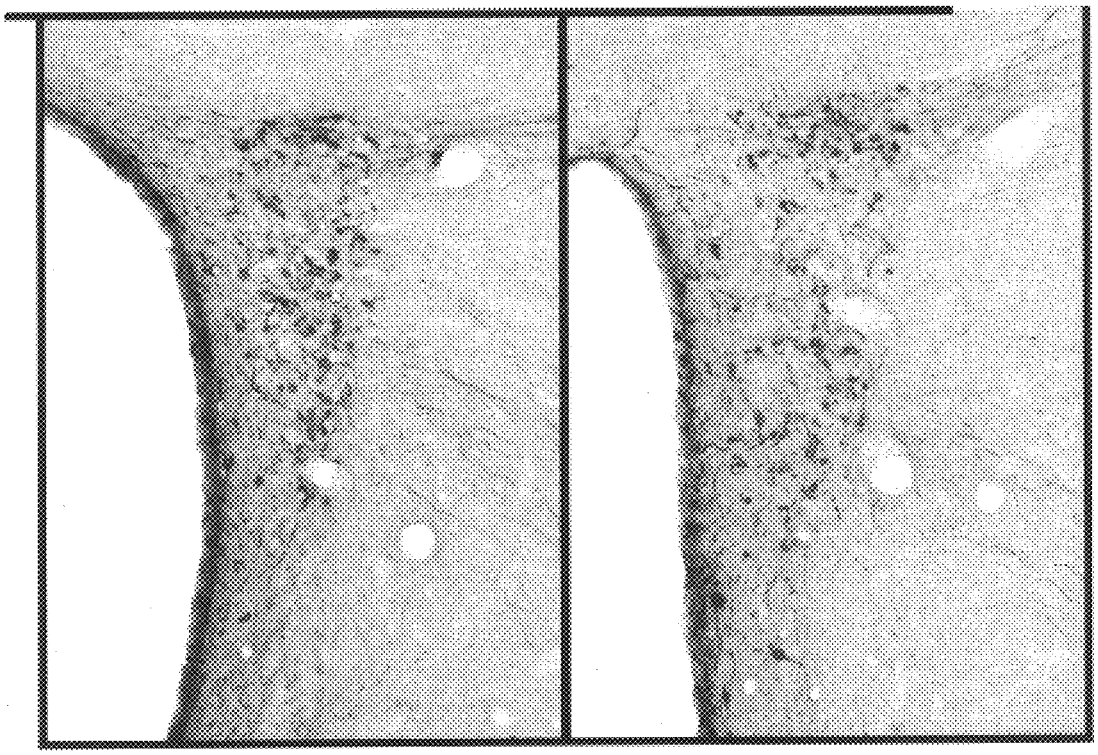

Corticotropin Releasing Factor Receptor-1 Deficient Mice Display an Impaired Endocrine Receptor-response to Stress The hormonal response to stress is triggered by increased corticotropin releasing factor secretion into the hypothalamic-pituitary-portal system by the paraventricular neurons of the hypothalamus, leading to increased ACTH secretion by pituitary corticotropes and the accompanying increase in corticosteroid secretion by the adrenal gland (Owens & Nemeroff, 1991). To determine whether the pituitary and adrenal response to stress was impaired in corticotropin releasing factor receptor-1 deficient animals, both male and female wild type and mutant mice were subjected to physical restraint stress for 10 minutes at 8:00 AM. Plasma concentrations of corticosterone and ACTH were measured in samples collected prior to and immediately after exposure to stress. Control animals, male and female, responded with a significant increase in ACTH and corticosterone secretion following physical restraint (FIG. 4A and 4B, respectively). In contrast, restraint stress did not lead to a measurable increase in circulating ACTH in the corticotropin releasing factor receptor-1 deficient mice (FIG. 4A) and the resulting increase in corticosterone also was greatly blunted in comparison to that of wild type mice (FIG. 4B). These results indicate that the endocrine response to stress is severely compromised in the corticotropin releasing factor receptor-1 deficient mice.

EXAMPLE 11

Corticotropin Releasing Factor Receptor-1 Mutant Mice Exhibit Reduced Anxiety

Figure 5A:
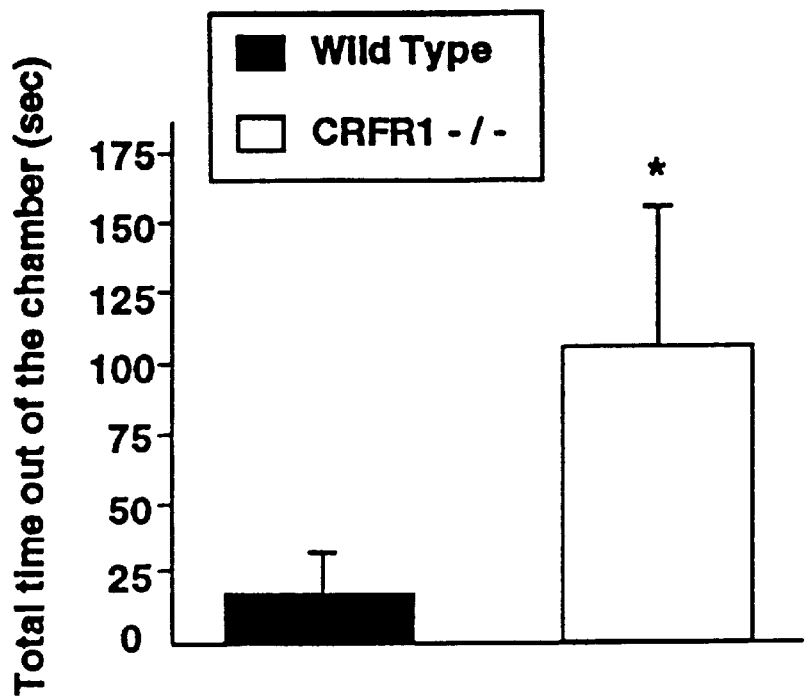
FIGS. 5A–5D show that corticotropin releasing factor receptor-1 deficient mice exhibited reduced anxiety. Behavior of corticotropin releasing factor receptor-1 deficient mice in the Dark-Light Emergence Task was determined and compared to control mice. Mice were placed into the small chamber at the start of the 5 minute session.

Adaptive changes indicative of anxiety are a major component of the stress response and a prominent role for corticotropin releasing factor in mediating the behavioral response to stress has been demonstrated (Koob, 1994). Therefore, mice lacking corticotropin releasing factor receptor-1 were evaluated for their behavioral response to stress. The behavioral responses of corticotropin releasing factor receptor-1 deficient mice to an anxiogenic environment were tested using a dark-light emergence task and compared to control mice. The mutant mice had a tendency to exit the small chamber into the open-field (aversive environment) with a shorter latency compared to the wild type mice and spent a significantly longer time in the open-field ($P<0.05$; FIG. 5A). The mean time spent in the open-field per exit was also greater for the mutant mice in comparison to that for the wild-type mice (19.9 ±7.53 versus 3.8±3.2 sec; $P<0.05$).

Figure 5B:
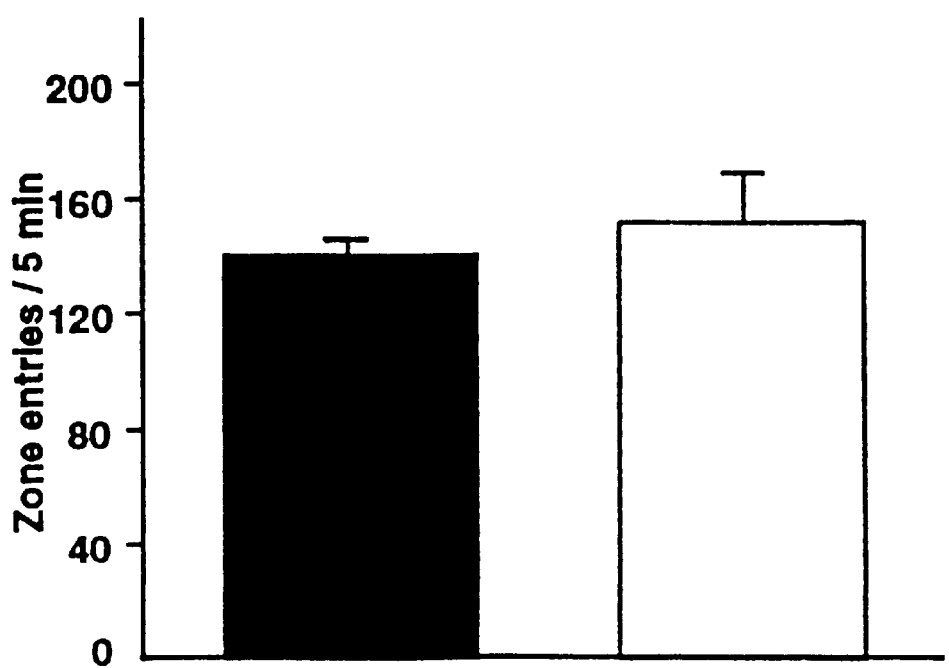

To verify that the reduced sensitivity of corticotropin releasing factor receptor-1 mutant mice to anxiogenic stimuli was not due to a difference in locomotor reactivity to novelty, locomotor activity was measured in a novel environment, under the same light conditions as for the dark-light emergence task. The total zone entries for the first 5 minutes (FIG. 5B), corresponding to the duration of the dark-light emergence protocol, as well as for the entire 3 hours test session were not different between the two groups. Therefore, differences in reactivity to novelty does not cause the increased tendency of mutant mice to exit the small chamber in the dark-light emergence task.

EXAMPLE 12

Figure 5C:
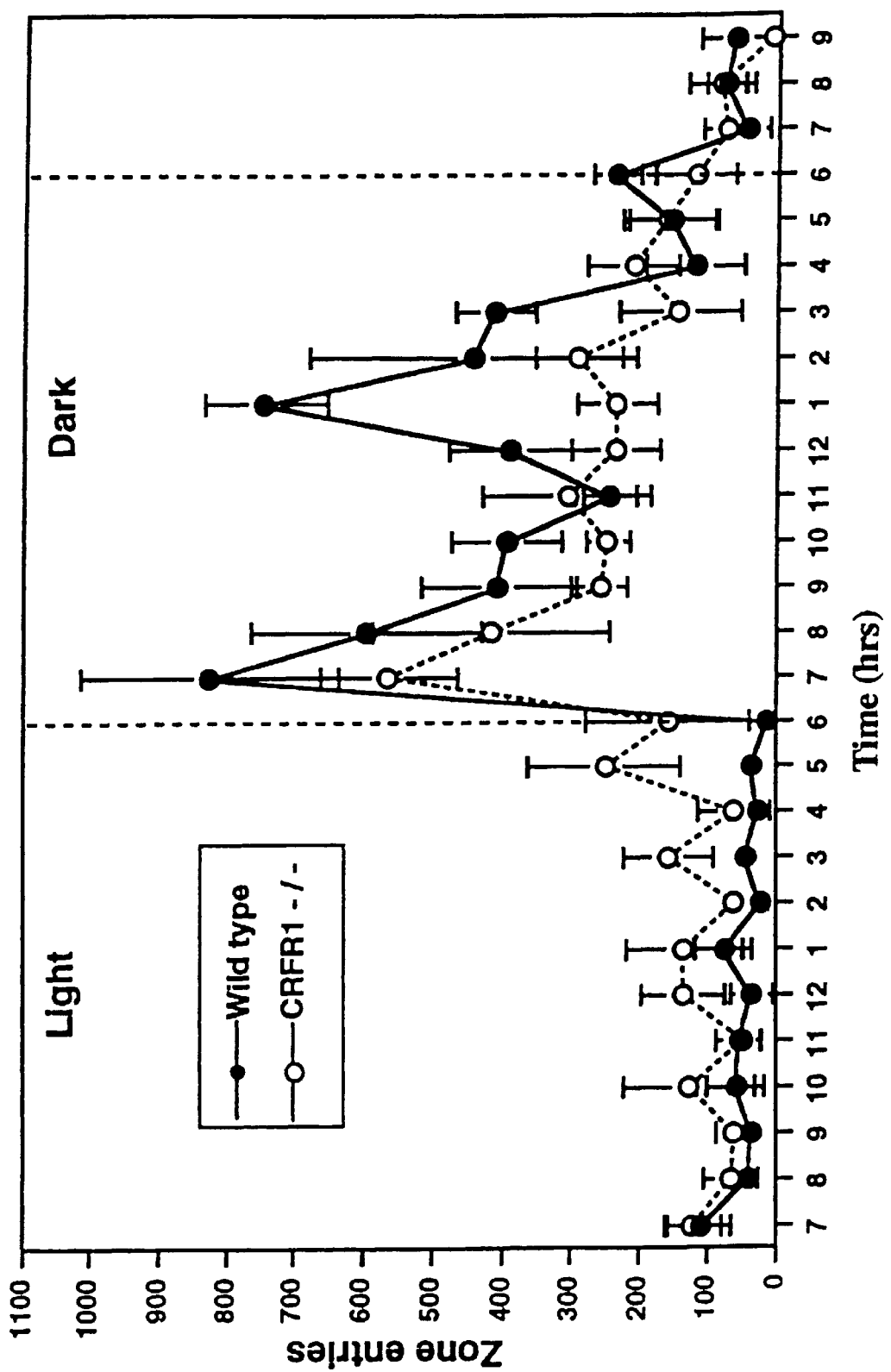
Figure 5D:
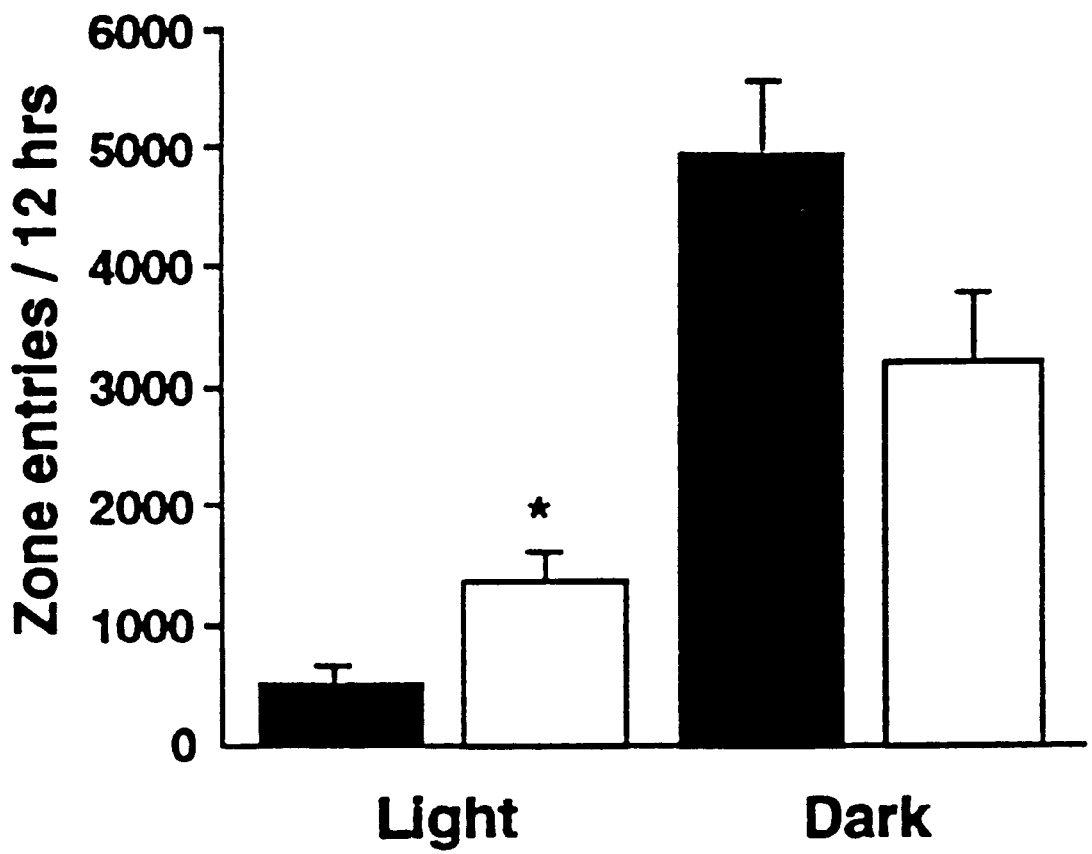

Corticotropin Releasing Factor Receptor-1 Deficient Mice Exhibit Altered Locomotor Activity Rhythms Circadian rhythms in both corticotropin releasing factor expression (Moldow & Fischman, 1984; Owens et al., 1990) and in several behavioral responses including locomotor activity have been clearly established. However, a potential role of the corticotropin releasing factor system in modulating rhythmic changes in behavior has not been determined. Therefore, the locomotor activity rhythms of corticotropin releasing factor receptor-1 deficient and wild type mice were characterized. Basal locomotor activity was evaluated over a 24 hour period consisting of 12 hour light and 12 hour dark following a period of habituation to the test apparatus (FIG. 5C). Both wild type and mutant mice exhibited the normal increase in activity during the dark phase as compared to the light phase of the cycle ($P<0.001$ and $P<0.01$ for wild type and mutant mice, respectively). However, locomotor activity of mutant mice was significantly higher than that of wild type mice during the light ($P<0.05$) but not during the dark phase of the cycle (FIG. 5D) and consequently, the percentage of increase in activity during the dark as compared to the light phase of the cycle was lower ($P<0.001$) in mutant mice (56.70±4.37) than in wild type mice (89.26±3.20). The increased activity of corticotropin releasing factor receptor-1 mutant mice was particularly evident during the last hours of the light cycle (FIG. 5C). Therefore, the corticotropin releasing factor receptor-1 mutant mice displayed altered locomotor activity rhythms manifest with increased activity during a time when wild type mice are normally less active.

EXAMPLE 13

Neonatal Mortality of the Progeny of Homozygous Corticotropin Releasing Factor Receptor-1 Mutant Females and In utero Rescue with Corticosterone As mentioned previously, the progeny born from heterozygous corticotropin releasing factor receptor-1 mutant mice were viable at birth and displayed a normal neonatal survival rate. To further characterize the reproductive and developmental capacity of the corticotropin releasing factor receptor-1 mutants, male and female homozygous mutant mice were intercrossed. While no markedly obvious differences in fertility of the corticotropin releasing factor receptor-1 mutants was observed, virtually all of the progeny born to homozygous corticotropin releasing factor receptor-1 mutant females died within 48 hours after birth.

Figures 6A, 6B, 6C:
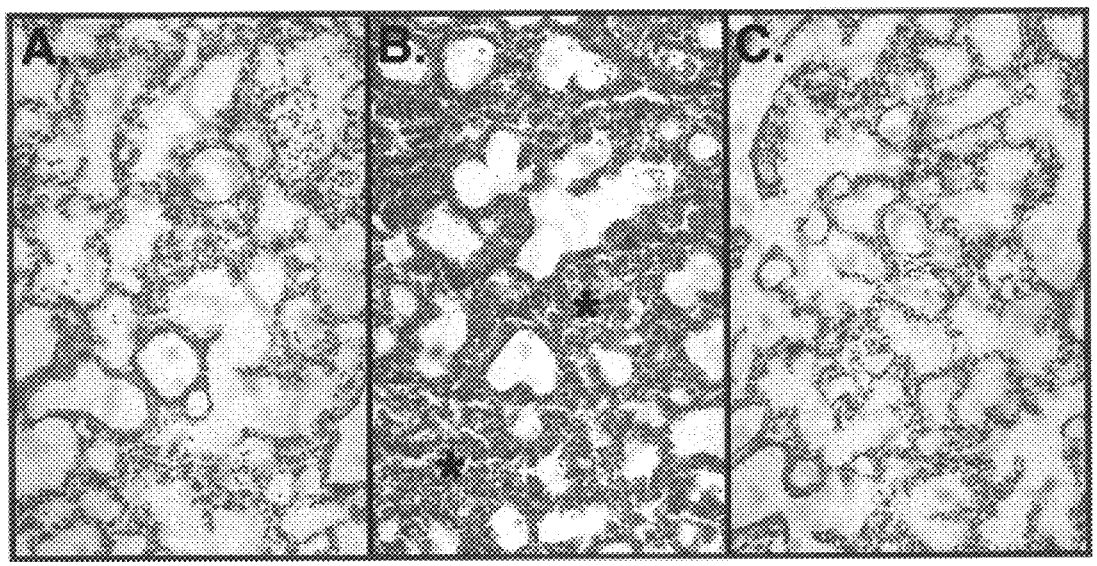
FIGS. 6A–6C show that the progeny of homozygous corticotropin releasing factor receptor-1 mutant females display a marked lung dysplasia that can be rescued by in utero treatment with corticosterone. Lungs from neonates at postnatal day 1 were fixed, sectioned and stained with hematoxylin and eosin.

Given the observed adrenal defect in mutant females and the well described requirement of corticosteroids for neonatal lung maturation (Ballard, 1989), these animals most likely died from respiratory distress after birth. Indeed, histological analysis of lungs collected on postnatal day 1 revealed a marked dysplasia of the lungs of offspring born to female homozygous mutant mice in comparison to those of pups born to control mice (FIG. 6A and 6B). Mutant lungs displayed alveolar collapse and reactive emphysema with intra-alveolar hemorrhage and hemosiderotic deposition (FIG. 6B). It was then determined whether corticosterone treatment can prevent the neonatal lung dysplasia and accompanying accentuated mortality of progeny born to homozygous mutant mice.

Results of these experiments indicated that in utero treatment of homozygous mutant females with corticosterone in the drinking water from embryonic day 12 through postnatal day 14 resulted in normal lung maturation in their progeny. Histological analysis of lungs collected on postnatal day 1 following in utero corticosterone treatment revealed a normal architecture, with thin alveolar septae and normal air space expansion (FIG. 6C). In utero corticosteroid treatment also resulted in a normal postnatal survival rate of progeny born to homozygous mutant females (data not shown). Together, these results and the fact that the neonatal survival rate of progeny born from intercross of heterozygous corticotropin releasing factor receptor-1 deficient mice is normal lead to the conclusion that the inadequate lung maturation and reduced postnatal survival of progeny born to homozygous corticotropin releasing factor receptor-1 mutant mice is a result of insufficient maternal corticosteroid production during late pregnancy and the neonatal period.

EXAMPLE 14
Hormonal Rescue of the Adrenal Defect in Corticotropin Releasing Factor Receptor-1 Mutant Mice Further characterization of the corticotropin releasing factor receptor-1 mutant mice was conducted to delineate the developmental and or endocrine basis for the marked adrenal atrophy of homozygous animals and whether the adrenal defect was first manifest during prenatal versus postnatal life. Given the absolute requirement of ACTH for maintenance of normal adrenal corticosteroid production (Colby et al., 1974), it was necessary to determine whether the adrenal atrophy was a direct result of a lack of corticotropin releasing factor receptor-1-dependent signaling pathways or is indirectly due to insufficient trophic hormone (ACTH) support during adrenal development.

Figure 7A:
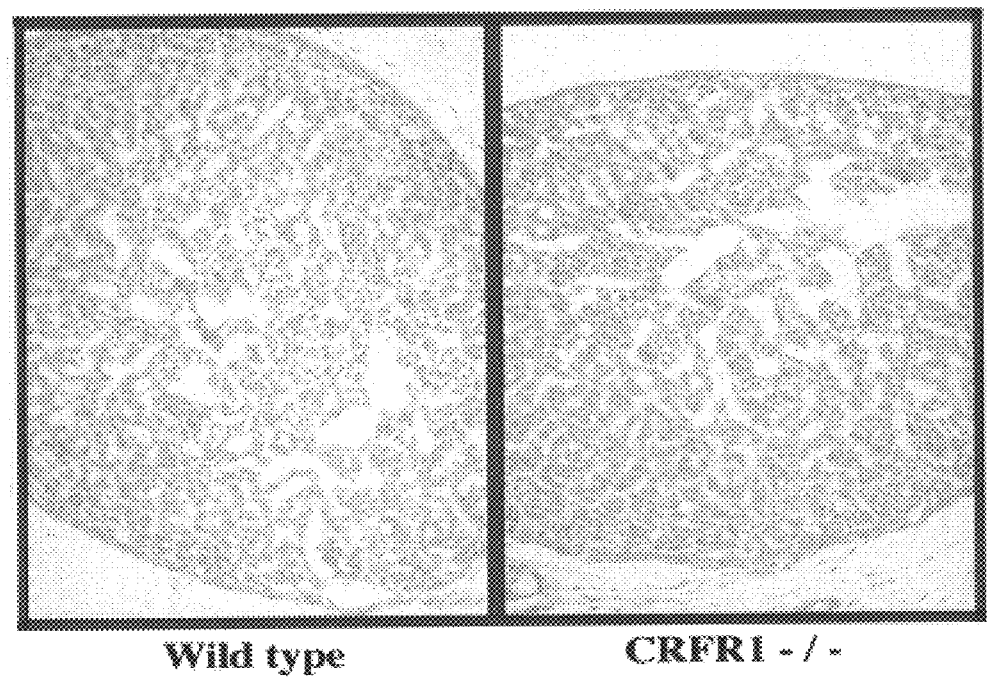
FIGS. 7A–7C show hormonal rescue of the adrenal defect in corticotropin releasing factor receptor-1 deficient mice.
Figure 7B:
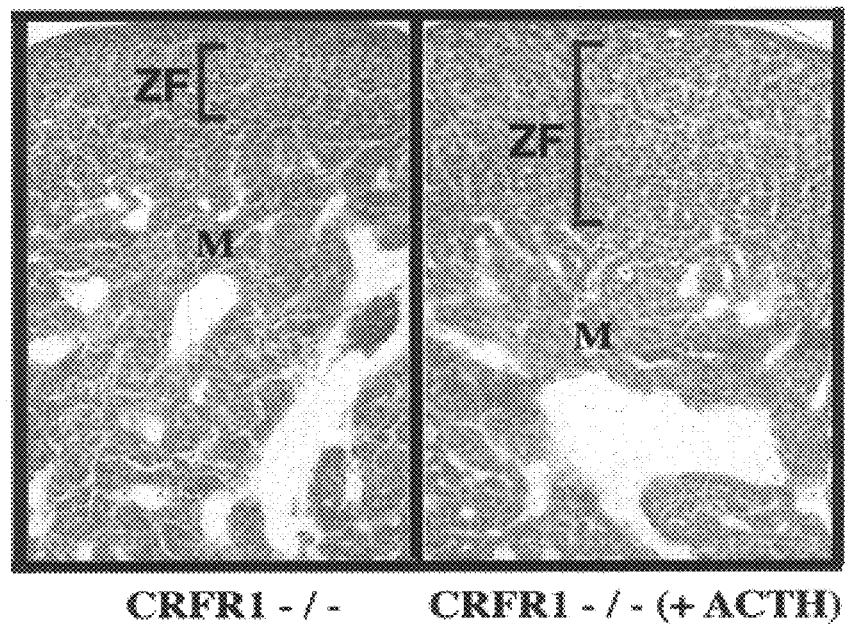

To assess whether the defect occurred during prenatal versus postnatal development, adrenal glands from control mice and from mutant mice were collected on postnatal day 3 and assessed histologically. No obvious differences in morphology of mutant adrenal glands were detected (FIG. 7A), indicating that the adrenal defect was manifest later during postnatal life. An ACTH treatment regime was then initiated to determine whether adrenal glands from mutant mice retain the capacity to respond to exogenous ACTH with a reduction in the atrophy of the zona fasciculata region. Twice daily injections of ACTH from postnatal days 10–21 resulted in an increase both in adrenal size and in the width of the zona fasciculata region in comparison to vehicle injected mutant mice (FIG. 7B). Hence, adrenal glands of the mutant mice do retain the capacity to respond to exogenous trophic hormone (ACTH) treatment. The adrenal defect may be a result of reduced circulating ACTH concentrations in the mutant mice during the period of normal postnatal adrenal maturation.

To verify that the mutant mice were deficient in ACTH during adrenal maturation, plasma samples were collected from homozygous mutant mice and wild type mice on postnatal day 10.

Figure 7C:
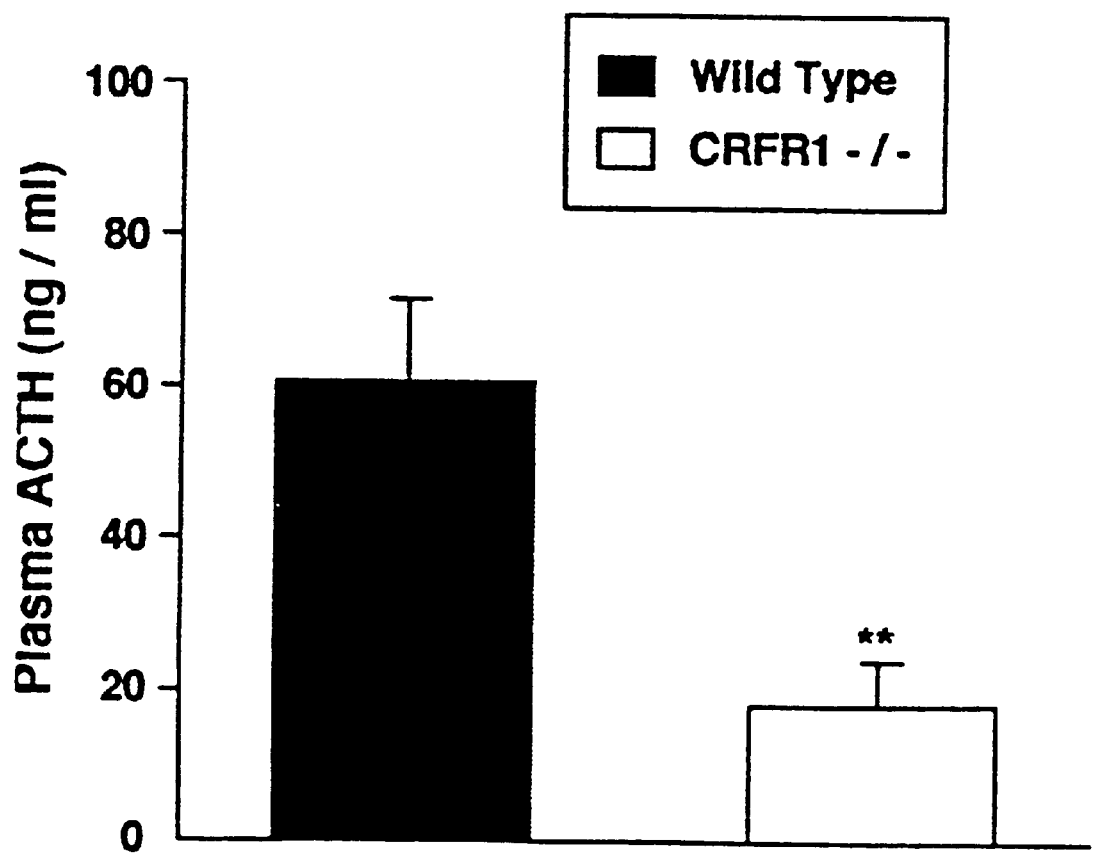

Assay of plasma ACTH concentrations revealed that the mutant mice have significantly lower ACTH concentrations on postnatal day 10 as compared to control mice (FIG. 7C; P<0.02). Therefore, the mechanism leading to the adrenal deficiency in mutant animals can likely be attributed to insufficient ACTH production during early postnatal life. These results suggest that corticotropin releasing factor receptor-1 mediated ACTH production by the pituitary gland is absolutely critical for normal postnatal development and maturation of the adrenal gland.

In the present invention, mice with a targeted disruption in the corticotropin releasing factor receptor-1 locus have been generated by gene targeting in embryonic stem cells. Cultured pituitary cells collected from mutant animals failed to display an increase in ACTH secretion upon corticotropin releasing factor treatment, verifying that the mutation resulted in loss of receptor function. Given the widespread distribution of corticotropin releasing factor receptor-1 within the brain and pituitary gland (Chalmers et al., 1995; Potter et al., 1994), and the temporal and spatial regulation of corticotropin releasing factor receptors observed during the prenatal and neonatal periods (Avishai-Eliner et al., 1996; Insel et al., 1988), one might have predicted that loss of corticotropin releasing factor receptor-1 mediated pathways would lead to pronounced developmental defects in the mutant animals. Indeed, corticotropin releasing factor receptor-1 deficient mice exhibited a pronounced atrophy of the zona fasciculata region of the adrenal gland. The observed adrenal defect manifested itself with markedly reduced circulating corticosterone concentrations in mature animals verifying both a structural and a functional abnormality in the corticotropin releasing factor receptor-1 mutants. Mice with a targeted disruption in the corticotropin releasing factor gene also exhibit a similar adrenal defect (Muglia et al., 1995).

Two potential explanations for the adrenal defect in these lines of mice can be proposed. Adrenal atrophy in the mutant mice may be indirect, due to a lack of corticotropin releasing factor stimulated ACTH secretion from the pituitary gland during development, or may be a direct result of ablation of a corticotropin releasing factor/corticotropin releasing factor receptor-1 dependent developmental pathway within the adrenal gland. Both corticotropin releasing factor and corticotropin releasing factor binding sites have been detected within the adrenal gland, but ligand and receptor expression is limited to the medullary region (Hashimoto et al., 1984; Suda et al., 1984; Udelsman et al., 1986). Corticotropin releasing factor treatment of cultured cells from the medullary region of the adrenal gland (chromaffin cells) promotes secretion of catecholamines and met-enkephalin (Udelsman et al., 1986). Although these factors have been reported to stimulate adrenocortical function in vitro (Kapas et al., 1995; Walker et al., 1988), blood flow within the adrenal gland travels from the cortex to the medulla (Udelsman et al., 1986). Therefore, it is unlikely that factors released from the adrenal medulla in response to corticotropin releasing factor can exert a trophic effect on adrenocortical maturation. These results clearly support the alternative hypothesis that the adrenal deficiency in corticotropin releasing factor receptor-1 mutant animals is mediated by insufficient ACTH secretion. The observed adrenal defect in corticotropin releasing factor receptor-1 deficient mice is both structurally and functionally similar to the adrenal defect observed following hypophysectomy. In hypophysectomized animals, ACTH replacement is absolutely required for maintenance of the zona fasciculata region (Idelman, 1970; Wyllie et al., 1973) and for normal corticosteroid production (Colby et al., 1974).

There appears to be a critical window of time during postnatal development when corticotropin releasing factor receptor-1 dependent ACTH secretion is absolutely required for full maturation of the adrenal gland. Manifestation of the adrenal defect during prenatal development of corticotropin releasing factor receptor-1 deficient mice seems unlikely.

Initial differentiation of the adrenal cortex occurs during prenatal life (Daikoku et al., 1976) and histological analysis of adrenal glands collected on postnatal day 3 revealed no detectable differences between the corticotropin releasing factor receptor-1 mutants and wild type mice. Therefore, the adrenal defect in corticotropin releasing factor receptor-1 mutant mice is likely manifest predominantly during postnatal life.

In the present study, plasma ACTH concentrations in mutant animals on postnatal day 10 were significantly lower than those in controls, and ACTH replacement from postnatal days 10–21 reversed the adrenal atrophy. However, circulating ACTH levels in mature mutant animals were similar to those of control mice. The fact that mutant animals are not subjected to the potent inhibitory effects of corticosterone on ACTH synthesis and secretion (Keller-Wood & Dallman, 1984) may account for the similar levels of ACTH in animals lacking corticotropin releasing factor receptor-1. However, the apparently normal circulating ACTH concentrations in mature mutant animals are not sufficient to restore maturation and normal function of the adrenal gland. Therefore, the adrenal defect appears to result from a lack of corticotropin releasing factor receptor-1 mediated ACTH secretion during early postnatal life.

In contrast to the adrenal defect, no anatomical defects within the brain and pituitary gland were detected in mutant animals. This result is somewhat surprising, given corticotropin releasing factor has been reported to be mitogenic for the ACTH producing cells of the pituitary in vivo (Gertz et al., 1987) and corticotropin releasing factor receptor-1 expression is initiated in distinct regions of the brain at specific times during development (Avishai-Eliner et al., 1996). Appearance and maturation of corticotropes was also normal in the corticotropin releasing factor deficient mice (Muglia et al., 1995). A critical requirement of corticotropin releasing factor/corticotropin releasing factor receptor-1 for normal corticotrope development, therefore, seems unlikely. However, a requirement for corticotropin releasing factor receptor-1 mediated ACTH production during early postnatal life has been established, because the corticotropin releasing factor receptor-1 mutant mice clearly display reduced circulating ACTH levels during the neonatal period.

Mutation of the corticotropin releasing factor receptor-1 gene was not accompanied by compensatory changes in the localization or level of expression of the second corticotropin releasing factor receptor subtype (corticotropin releasing factor receptor-2). However, a compensatory increase in expression of the predominant ligand for corticotropin releasing factor receptor-1 was detected within the PVN of corticotropin releasing factor receptor-1 deficient mice. The increase in corticotropin releasing factor mRNA and protein was limited to the PVN and not detected in other corticotropin releasing factor producing regions of the brain such as the amygdala. The increased expression of corticotropin releasing factor receptor-1 in the PVN may be mediated by the reduced negative feedback effects of corticosteroids. In rats, both corticotropin releasing factor and arginine vasopressin expression in the PVN are inhibited by corticosteroids (Sawchenko, 1987) and elevated by adrenalectomy (Sawchenko et al., 1984). However, expression of arginine vasopressin (another key regulator of ACTH secretion) in the PVN of corticotropin releasing factor receptor-1 deficient mice was similar to that of control animals. Regardless, the normal circulating ACTH levels of mature mutant mice cannot be accounted for by increased arginine vasopressin stimulation of corticotrope function.

Corticotropin releasing factor receptor-1 mutant females were fertile and exhibited no obvious reproductive abnormalities. Progeny born to heterozygous mutant females displayed normal neonatal survivability, while progeny born to homozygous mutant females died within forty eight hours after birth due to lung dysplasia. A similar etiology and neonatal mortality was reported for both the corticotropin releasing factor deficient mice (Muglia et al., 1995) and for mice with a targeted disruption in the glucocorticoid receptor gene (Cole et al., 1995). In the progeny of homozygous corticotropin releasing factor receptor-1 mutant females, the neonatal mortality was a result of maternal corticosterone deficiency leading to inadequate fetal/neonatal lung maturation. In the present invention, survival of offspring was restored by corticosterone supplementation beginning in utero. A similar paradigm was used to rescue progeny born to homozygous corticotropin releasing factor mutant mice (Muglia et al., 1995) and corticosteroid treatment is commonly used to treat respiratory distress syndrome of prematurely born children (Ballard, 1989).

To investigate the behavioral consequences of corticotropin releasing factor receptor-1 deficiency, wild-type and corticotropin releasing factor receptor-1 mutant mice were compared in a dark-light emergence task consisting of a free-choice response to a stressful environment. Corticotropin releasing factor receptor-1 mutant mice visited the illuminated open-field for a longer time than did the wild-type mice. Thus, the mutant mice showed an increased approach to an environment generally considered as aversive in rodents (Archer, 1973; Crawley & Goodwin, 1980; Denenbergh, 1967; Misslin, 1989) and were less sensitive to this anxiogenic-1 like stimulus. Acute locomotor activity of corticotropin releasing factor receptor-1 mutant mice when tested in a novel environment was not different from control mice, indicating that the reduced anxiety of mutant animals was not due to a difference in reactivity to novelty. Prior studies have demonstrated that the anxiogenic-like effects of corticotropin releasing factor in rats are independent of activation of the pituitary-adrenal axis (Britton et al., 1986). Previous data in rats injected centrally with corticotropin releasing factor antagonists and antisense oligonucleotides also suggests that the behavioral and physiological responses to stress may depend on corticotropin releasing factor actions in the brain system (Martinez et al., 1997; Skutella et al., 1994; Swiergiel et al., 1993, Takahashi et al., 1989). In addition, treatment of rats with the nonpeptide corticotropin releasing factor receptor antagonist CP-154, 526, with a high selectivity for corticotropin releasing factor receptor-1, has also been reported to inhibit the anxiogenic effects of centrally administered corticotropin releasing factor (Schulz et al., 1996). Therefore, the reduced anxiogenic response of corticotropin releasing factor receptor-1 mutant mice likely was not due to their altered corticosterone profiles. Taken together, these results indicate that an attenuation of corticotropin releasing factor activity facilitates exploration under stressful conditions. These results are consistent with the current literature showing that central administration of corticotropin releasing factor initiates behavioral responses to stress (Berridge & Dunn, 1986; Koob, 1994; Morimoto et al., 1993; Takahashi et al., 1989, Liang et al., 1992) and clearly demonstrate that corticotropin releasing factor dependent pathways involved in the behavioral response to stress are mediated by corticotropin releasing factor receptor-1.

Although circadian changes in both hypothalamic corticotropin releasing factor concentrations (Moldow & Fischman, 1984; Owens et al., 1990) and behavioral responses such as locomotor activity have been well established, a functional role of corticotropin releasing factor dependent pathways in modulation of rhythmic locomotor activity has not been demonstrated. The rhythmic cycle of locomotor activity is affected by the mutation in the corticotropin releasing factor receptor-1 deficient mice. These animals have a less pronounced rhythm of activity between dark and light periods as compared to wild type animals, apparently due to an increase in activity during the light phase of the light-dark cycle. At this point, an effect of chronic corticosteroid deficiency on the rhythmic cycle of locomotor activity in the corticotropin releasing factor receptor-1 mutant mice cannot be ruled out and will require further investigation. However, this seems unlikely because previous studies in rats demonstrated that adrenalectomy has no effect on locomotor activity during the light phase (Iuvone & Van Hartesveldt, 1977).

While two specific corticotropin releasing factor receptor subtypes have been described to date, the precise role these receptors play in mediating the biological responses to corticotropin releasing factor or corticotropin releasing factor related ligands under both undisturbed and stressful conditions have not been completely elucidated. Corticotropin releasing factor receptor-1 expression within both the brain and pituitary gland is clearly regulated by stress (Rabadan-Diehl et al., 1996; Rivest et al., 1995) and by corticotropin releasing factor and other modulators (Mansi et al., 1996; Pozzoli et al., 1996) while expression of corticotropin releasing factor receptor-2 is constitutive under similar conditions (Rivest et al., 1995). These results raise the possibility that corticotropin releasing factor receptor-1 is the major stress receptor within the brain for corticotropin releasing factor.

In the present experiments, it was clearly demonstrated that the classical endocrine and behavioral responses to stress are mediated by corticotropin releasing factor receptor-1. However, the stress induced reduction of serum testosterone concentrations was not diminished in male corticotropin releasing factor receptor-1 mutant mice, indicating that the adaptive responses of an animal to stress are not mediated solely through corticotropin releasing factor receptor-1. Additional studies can precisely determine which of the other responses to stress are mediated by corticotropin releasing factor receptor-1 and to determine the role of corticotropin releasing factor receptor-1 mediated pathways in cognitive function. Further clarification of the precise role of each corticotropin releasing factor receptor subtype may lead to the development and application of specific corticotropin releasing factor receptor antagonists for treatment and or diagnosis of various neuropsychiatric disorders and for improvement of learning and memory in cases of dementia.

The following references were cited herein:

Archer, J. (1973). Anim. Behav. 21, 205–235.
Avishai-Eliner, et al. (1996). Brain Res. Dev. Brain Res. 91, 159–163.
Ballard, P. L. (1989). Endocr. Rev. 10, 165–181.
Behan, D. P., et al. (1995). Nature 378, 284–287.
Berridge, C. W., et al. (1986). Regul. Pept. 16, 83–93.
Britton, K. T., et al. (1986). Life Sci. 39, 1281–1286.
Chalmers, D. T., et al. (1995). J. Neurosci. 15, 6340–6350.
Chan, receptor-. K., et al. (1993). J. Neurosci. 13, 5126–5138.
Chrousos, G. P., et al. (1992). J. Am. Med. Assoc. 267, 1244–1252.
Colby, H. D., et al. (1974). Endocrinology 94, 1346–50.
Cole, T. J., et al. (1995). Genes Dev. 9, 1608–1621.
Crawley, J., et al. (1980). Pharmacol. Biochem. Behav. 13, 167–170.
Daikoku, S., et al. (1976). Cell Tissue Res. 168, 549–59.
De Souza, E. B. (1995). Psychoneuroendocrinology 20, 789–819.
Denenbergh, V. (1967). In Biology and Behavior: Neurophysiology and Emotion, D. Glass, ed. (New York: Rockefeller University Press and Russell Sage Foundation), pp. 161–190.
Diamant, M., et al. (1993). Neuroendocrinology 57, 1071–81.
Gertz, B. J., et al. (1987). Endocrinology 120, 381–388.
Grigoriadis, D. E., et al. (1996). Ann. N. Y. Acad. Sci. 780, 60–80.
Hashimoto, K., et al. (1984). Peptides 5, 707–711.
Idelman, S. (1970). Int. Rev. Cytol. 27, 181–281.
Insel, T. R., et al. (1988). J. Neurosci. 8, 4151–4158.
Iuvone, P. M. et al. (1977). Behav Biol 19, 228–237
Kapas, S., et al. (1995). J. Endocrinol. 144, 503–510.
Keller-Wood, M. E., et al. (1984). Endocr. Rev. 5, 1–24.
Kishimoto, T., et al. (1995). Proc. Natl. Acad. Sci. USA 92, 1108–1112.
Koob, G., et al. (1994). Semin. Neurosci. 6, 221–229.
Koob, G. F., et al. (1985). Fed. Proc. 44, 259–63.
Lee, K. F., et al. (1992). Cell 69, 737–749.
Liang, K. C., et al. (1988). Psychopharmacology (Berl) 96, 232–6.
Liang, K. C., et al. (1992). J Neurosci. 12, 2303–2312.
Lovenberg, T. W., et al. (1995). Endocrinology 136, 4139–4142.
Mansi, J. A., et al. (1996). Endocrinology 137, 4619–4629.
Martinez, V., et al. (1997). J. Pharmacol. Exp. Ther. 280, 754–760.
Misslin, R., et al. (1989). Behav. Process. 18, 119–132.
Moldow, R L., et al. (1984). Peptides 5, 1213–1215.
Morimoto, A., et al. (1993). J. Physiol. (Lond) 460, 221–229.
Muglia, L., et al. (1995). Nature 373, 427–432.
Orth, D. N. (1992). Endocr. Rev. 13, 164–191.
Owens, M. J., et al. (1990). Neuroendocrinology 52, 626–631.
Owens, M. J., et al. (1991). Pharmacol. Rev. 43, 425–473.
Perrin, M., et al. (1995). Proc. Natl. Acad. Sci. USA 92, 2969–2973.
Potter, E., et al. (1994). Proc. Natl. Acad. Sci. USA 91, 8777–8781.
Pozzoli, G., et al. (1996). Endocrinology 137, 65–71.
Rabadan-Diehl, C., et al. (1996). Endocrinology 137, 3808–3814.
Rivest, S., et al. (1995). J. Neurosci. 15, 2680–2695.
Sawchenko, P. E. (1987). J. Neurosci. 7, 1093–1106.
Sawchenko, et al. (1984). Proc. Natl. Acad. Sci. USA 81, 1883–1887.
Schulz, D., et al. (1996). Proc. Natl. Acad. Sci. USA 93, 10477–10482.
Segre, G. V., et al. (1993). Trends Endocrinol. Metab. 4, 309–314.
Skutella, T., et al. (1994). Neuroreport 5, 2181–2185.
Spina, M., et al. (1996). Science 273, 1561–1564.
Stenzel, P., et al. (1995). Mol. Endocrinol. 9, 637–645.
Suda, T., et al. (1984). J. Clin. Endocrinol. Metab. 58, 919–924.
Swiergiel, A. H., et al. (1993). Brain Res. 623, 229–234.
Takahashi, L. K., et al. (1989). Behav. Neurosci. 103, 648–654.
Turnbull, A. V., et al. (1996). Eur. J. Pharmacol. 303, 213–216.
Udelsman, R, et al. (1986). Nature 319, 147–150.
Vale, W., et al. (1981). Science 213, 1394–1397.

Vale, W., et al. (1997). The Endocrinologist 7, 3S–9S.

Vale, W., et al. (1983). In Methods in Enzymology: Neuroendocrine Peptides, P. M. Conn, ed. (New York: Academic Press), pp. 565–577.

Vaughan, J., et al. (1995). Nature 378, 287–292.

Walker, S. W., et al. (1988). Mol. Cell. Endocrinol. 57, 139–147.

Wyllie, A. H., et al. (1973). J. Pathol. 111, 85–94.

Xu, M., et al. (1994). Cell 79, 729–742.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended a s limitations on the scope of the invention. Changes therein and other uses will occur to those skilled in the art which are encompassed within the spirit of the invention as defined by the scope of the claims.

What is claimed:

1. A transgenic mouse whose somatic and germ cells have a substantial deficiency in the corticotropin releasing factor receptor-1, wherein both alleles of the corticotropin releasing factor receptor-1 are disrupted resulting in a mouse with decreased anxiety, reduced endocrine response to stress and increased locomoter activity rhythms as compared to a control mouse.

2. A method of identifying an agonist of corticotropin releasing factor, urocortin, or a ligand in the corticotropin releasing factor family that acts through receptors other than corticotropin releasing factor receptor-1, comprising the steps of:
    a) administering a test compound or a placebo compound to a transgenic mouse of claim 1;
    b) administering a corticotropin releasing factor, urocortin, or a ligand in the corticotropin releasing factor family to a wild type mouse;
    c) determining the level of anxiety, the endocrine response to stress, and the locomoter activity rhythms in both the transgenic and the wild type mice; and
    d) comparing the level of anxiety, the endocrine response to stress, and the locomoter activity rhythms in, wherein effects caused by said test compound, and not by said placebo, that mimic the effects caused by a corticotropin releasing factor, urocortin, or a ligand in the corticotropin releasing factor family are indicative of an agonist of a corticotropin releasing factor, urocortin, or a ligand in the corticotropin releasing factor family acting through a receptor other than corticotropin releasing factor receptor-1.

3. The method of claim 2 wherein said receptor other than corticotropin releasing factor receptor-1 is selected from the group consisting of corticotropin releasing factor receptor-2 and a receptor in the corticotropin releasing factor receptor family.

4. A method of identifying an antagonist of corticotropin releasing factor, urocortin, or a ligand in the corticotropin releasing factor family that acts through a receptor other than corticotropin releasing factor receptor-1, comprising the steps of:
    a) administering a test compound or a placebo compound to a transgenic mouse of claim 1;
    b) administering a corticotropin releasing factor, urocortin, or a ligand in the corticotropin releasing factor family to a transgenic mouse of claim 1,
    c) determining the effects of the test compound, the placebo, and the corticotropin releasing factor, urocortin, or a ligand in the corticotropin releasing factor family, on the level of anxiety, the endocrine response to stress, and the locomoter activity rhythms in each mouse; and
    d) comparing the levels of anxiety, the endocrine responses to stress, and the locomoter activity rhythms in each mouse, wherein a test compound is deemed to be an antagonist if it causes effects not caused by the placebo, wherein said effects are opposite to those caused by corticotropin releasing factor, urocortin, or a ligand in the corticotropin releasing factor family.

5. The method of claim 4, wherein said receptor other than corticotropin releasing factor-1 is selected from the group consisting of corticotropin releasing factor receptor-2 and a receptor in the corticotropin releasing factor receptor family.

6. A method of screening compounds that are analogs or agonists of corticosterone or corticotropin, comprising the steps of:
    a) performing a mating between a homozygous female mouse of claim 1 and a homozygous male mouse of claim 1;
    b) administering a pharmaceutically acceptable dose of said compound to said female mouse post-conception; and
    c) determining the histological condition of the lungs of progeny born to said female mouse, wherein an absence of displaysia, alveolar collapse and reactive emphysema with intraalveolar hemorrhage and hemosiderotic deposition is indicative of an analog or agonist of corticosterone or corticotropin.

7. The progeny of a mating between a mouse of claim 1 and a mouse of another strain, wherein both alleles of the corticotropin releasing factor receptor-1 are disrupted in said mouse of another strain.

8. A method of producing a transgenic mouse in whose genome one or both alleles of the corticotropin releasing factor receptor-1 gene have been disrupted, said method comprising:
    a) producing positive ES cells by introducing a corticotropin releasing factor receptor-1 transgene derived from a mouse corticotropin releasing factor receptor-1 gene into embryonic stem cells, said transgene comprising a gene encoding a selectable marker in place of exon 5 through exon 8 of said corticotropin releasing factor receptor-1 gene, wherein ES cells that survive and grow under selection for said selectable marker are positive ES cells;
    b) introducing said positive ES cells into C57BL/6 blastocysts;
    c) transferring said blastocysts into pseudopregnant mice; and
    d) identifying transgenic progeny in which one or both alleles of the endogenous corticotropin releasing factor receptor-1 gene have been disrupted.

9. The method of claim 8 further comprising the step of mating said transgenic mice to produce a transgenic mouse which is homozygous for said transgene.

10. A transgenic mouse that can be used in matings to generate the mouse of claim 1, wherein one allele of corticotropin releasing factor receptor-1 is disrupted in somatic and germ cells of said mouse.

* * * * *

UNITED STATES PATENT AND TRADEMARK OFFICE
CERTIFICATE OF CORRECTION

PATENT NO. : 6,147,275
DATED : November 14, 2000
INVENTOR(S) : Wylie Vale and Kuo-Fen Lee It is certified that error appears in the above-identified patent and that said Letters Patent is hereby corrected as shown below:

Column 1,
Before the caption "BACKGROUND OF THE INVENTION" please insert the following paragraph:
-- The file of this patent contains at least one drawing executed in color. Copies of this patent with color drawing(s) will be provided by the Patent and Trademark Office upon request and payment of the necessary fee. --.

Column 6,
Line 48, "specicif" should read -- specific --.

Column 7,
Line 16, "b e" should read -- be --.
Line 19, please insert the word -- of -- between "use" and "the".

Column 8,
Line 9, "vectors" should read -- vector --.

Column 10,
Line 47, please remove the word "were".

Column 11,
Line 37, "forty five" should read -- forty-five --.

Column 16,
Line 8, "does" should read -- do --.

Column 23,
Line 22, "a s" should read -- as --.
Line 40, please remove the space before "administering".
Line 56, please insert a comma after "claim 2".

UNITED STATES PATENT AND TRADEMARK OFFICE
CERTIFICATE OF CORRECTION

PATENT NO. : 6,147,275
DATED : November 14, 2000
INVENTOR(S) : Wylie Vale and Kuo-Fen Lee It is certified that error appears in the above-identified patent and that said Letters Patent is hereby corrected as shown below:

Column 24,
Line 17, please insert the word -- receptor -- between "factor and "-1 is".

Signed and Sealed this

Thirteenth Day of November, 2001

Attest:

*Nicholas P. Godici*

NICHOLAS P. GODICI
*Attesting Officer*      *Acting Director of the United States Patent and Trademark Office*